United States Patent [19]

Arai et al.

[11] 4,040,836
[45] Aug. 9, 1977

[54] SILVER HALIDE EMULSION CONTAINING TWO-EQUIVALENT COUPLER

[75] Inventors: Atsuaki Arai; Kotaro Nakamura; Minoru Yamada; Nobuo Furutachi, all of Minami-ashigara, Japan

[73] Assignee: Fuji Photo Film Co., Ltd., Minami-ashigara, Japan

[21] Appl. No.: 597,280

[22] Filed: July 18, 1975

[30] Foreign Application Priority Data

July 18, 1974 Japan .................................. 49-82415

[51] Int. Cl.$^2$ .......................... G03C 7/00; G03C 1/40
[52] U.S. Cl. ..................................... 96/56.5; 96/56.6; 96/74; 96/100; 548/324; 548/360; 548/361
[58] Field of Search ....................... 96/100, 56.5, 56.6, 96/74; 260/310 A

[56] References Cited

U.S. PATENT DOCUMENTS

| 3,212,894 | 10/1965 | Menzel et al. | 96/56.6 |
|---|---|---|---|
| 3,576,636 | 4/1971 | Matsui et al. | 96/100 |
| 3,622,328 | 11/1971 | Pollet et al. | 96/100 |
| 3,649,278 | 3/1972 | Iwama et al. | 96/100 |

*Primary Examiner*—J. Travis Brown
*Attorney, Agent, or Firm*—Sughrue, Rothwell, Mion, Zinn and Macpeak

[57] ABSTRACT

A photographic two-equivalent magenta coupler represented by the following general formula (I):

$$A-S(O)_n-R \qquad (I)$$

wherein A represents a residue of a magenta color image forming coupler in which one of the hdyrogen atoms on the active methylene group is eliminated; R represents an alkyl group, an aryl group or a heterocyclic group; and n represents 1 or 2; and color photographic light-sensitive material containing the two-equivalent magenta coupler.

10 Claims, No Drawings

SILVER HALIDE EMULSION CONTAINING TWO-EQUIVALENT COUPLER

BACKGROUND OF THE INVENTION

1. Field of the Invention

The present invention relates to color photography and more particularly, it relates to a novel class of two-equivalent megenta couplers which are suitable for use in silver halide color photographic light-sensitive materials.

2. Description of the Prior Art

It is known that, by the color development of a silver halide color photographic material, a color developing agent of an aromatic primary amine type is oxidized and is reacted with a coupler to from a dye, such as an indophenol, an indoaniline, an indamine, an azomethine, a phenoxazine, a phenazine and the like, thus forming a color image. In this type, the subtractive color process is ordinarily used for color reproduction and yellow, magenta and cyan color images are formed, which are respectively the complementary colors of blue, green and red. For example, a coupler of the acylacetanilide or dibenzoylmethane type is used for forming a yellow color image, a coupler of the pyrazolone, cyanoacetophenone or indazolone type is used for forming a magenta color image and a coupler of the phenol type, such as a phenol and a naphthol, is used for forming a cyan color image.

In one of the most preferred embodiments of the color photographic light-sensitive materials, the dye image forming couplers are incorporated into a silver halide emulsion. These couplers which are incorporated into the emulsion must be non-diffusible (diffusion resistant) in the binder matrix of the emulsion.

The color image forming couplers of the prior art are almost all four-equivalent couplers which require theoretically four moles of silver halide as an oxidizing agent for forming one mole of the dye through the coupling reaction. On the contrary a two-equilvalent coupler having an active methylene group which is substituted by a group capable of being released through the coupling of an oxidized product of an aromatic primary amino developing agent requires only the development of two moles of silver halide for forming one mole of the dye. Since the quantity of silver halide required for forming a dye with a two-equivalent coupler is one half of that required with an ordinary four-equivalent coupler many advantages are achieved with a two-equivalent coupler in that a thinner light-sensitive layer can be used and the layer can be processed rapidly. In addition, the photographic properties and economy can increased through a reduction in the layer thickness using a two-equivalent coupler.

Several attempts have been made to convert 5-pyrazolone type couplers, which have been conventionally used as a magenta color forming coupler, to two-equivalent couplers by substituting one of the hydrogen atoms at the 4-position of the 5-pyrazolone with a group capable of being split off. For example, in such couplers the 4-position of the pyrazolone is substituted with a thiocyano group as described in U.S. Pat. Nos. 3,214,437 and 3,253,924, an acyloxy group as described in U.S. Pat. No. 3,311,476, an aryloxy group as described in U.S. Pat. No. 3,419,381, a 2-triazolyl group as described in U.S. Pat. No. 3,617,291, a halogen atom as described in U.S. Pat. No. 3,522,052, and the like.

However, when these 4-position substituted pyrazolone couplers are employed, some disadvantages occur in that a remarkable color fog is produced, in that the coupling reactivity is insufficient, in that the couplers per se are chemically unstable and change into compounds which can not form dyes or in that many difficulties are encountered during the preparation thereof.

The substitution of the 4-position of the 5pyrazolones with an alkylthio group, an arylthio group or a heterocyclic thio group is also known as described in U.S. Pat. No. 3,227,554. However most of these known thio-substituted pyrazolone compounds have the disadvantages that their reactivity with the oxidation products of an aromatic primary amine color developing agent is low, that the mercapto compounds which are formed upon the coupling reaction have such severe photographic effects that they can not be used in a conventional color photographic light-sensitive materials, and that the couplers are chemically unstable.

On the other hand, as couplers which can be used in a color developer solution, four-equivalent couplers have the disadvantage that a greater amount of silver halide is required to obtain a certain color image density, and the previously known two-equivalent couplers can not provide preferred results since the couplers are not sufficiently stable in a color developer solution.

SUMMARY OF THE INVENTION

Therefore, an object of the present invention is to provide a novel two-equivalent magenta color image forming coupler in which the coupling position of the magenta coupler is substituted with a group capable of being released by the coupling reaction with oxidation product of an aromatic primary amine developing agent.

Another object of the present invention is to provide a novel two-equivalent magenta coupler which has a suitable reactivity and which is capable of forming a dye in a high yield and without forming undesired stains and fog.

Another object of the present invention is to provide a novel two-equivalent magenta coupler which has an improved conversion rate to a dye, an excellent resistance to the effects of chemical compounds and a good coupling reactivity.

Still another object of the present invention is to provide a novel two-equivalent magenta coupler which can be prepared in a simple manner and in a high yield.

Still another object of the present invention is to provide a color photographic light-sensitive material having a silver halide emulsion layer containing a novel magenta color image forming coupler.

A further object of the present invention is to provide a method whereby the amount of the silver halide in the photographic emulsion layer is reduced and the sharpness of the color image obtained is improved by the use of a novel magenta color image forming coupler.

An even further object of the present invention is to provide a color photograph having a durable color image by the use of a novel magenta color image forming coupler.

A still further object of the present invention is to provide a method of forming a dye image by processing a silver halide photographic light-sensitive material with a color developer solution containing a novel two-equivalent magenta coupler in which the coupling position of the magenta color image forming coupler is substituted with a group capable of being released by the coupling reaction with an oxidation product of an aromatic primary amine developing agent.

These and other objects of the present invention will become apparent from the following detailed description and examples.

These objects of the present invention are accomplished with a two-equivalent magenta coupler, capable of forming a magenta color image upon coupling reaction with an oxidation product of an aromatic primary amine developing agent, represented by the general formula (I)

$$A — S(O)_n — R \quad (I)$$

wherein A represents a residue of a magenta color image forming coupler in which one of the hydrogen atoms on the active methylene group is eliminated, i.e., the $—S(O)_n—$ moiety is bonded to the coupling position; R represents an alkyl group, an aryl group or a heterocyclic group; and n represents 1 or 2.

DETAILED DESCRIPTION OF THE INVENTION

The magenta color image forming couplers described above include various types of compounds, for example, 5-oxo-2-pyrazolines, cyanoacetylcoumarins, and the like. Of these types, 5-oxo-2-pyrazoline and pyrazolo-[1,5-a]-benzimidazole magenta color image forming couplers are preferred.

Particularly preferred couplers of the present invention having the general formula (I) are those represented by the following general formulae (II) and (III)

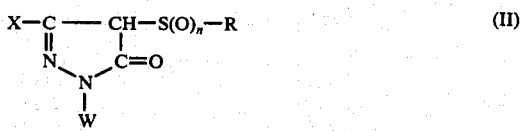

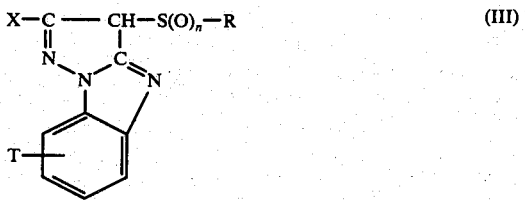

In the above general formulae, W represents a hydrogen atom; or has up to 40 carbon atoms, preferably up to 22 carbon atoms. Suitable examples of groups of W include a straight chain or branched chain alkyl group (e.g., a methyl, ethyl, isopropyl, tert-butyl, hexyl, dodecyl, docosyl, etc., group), an alkenyl group (e.g., an allyl, β-vinylethyl, etc., group), a cycloalkyl group (e.g., a cyclohexyl, norbornyl, 7,7-dialkylnorbornyl, 2-pentadecyl-7,7-dialkylnorbornyl, etc., group) an aralkyl group (e.g., a benzyl,β-phenylethyl, etc., group) or a cyclalkenyl group (e.g., a cyclopentenyl, cyclohexenyl, etc., group) and these groups as described above can be substituted with one or more of a halogen atom (e.g., a chlorine, bromine, fluorine, et., atom), nitro group, a cyano group, an aryl group (e.g., a phenyl, tolyl, methoxyphenyl, naphthyl, etc., group) an alkoxy group (e.g., a methoxy, butoxy, octyloxy, etc., group), an aryloxy group (e.g., a phenoxy, tolyloxy, naphthoxy, etc., group), a carboxyl group, an alkylcarbonyl group (e.g., a methylcarbonyl, octylcarbonyl, etc., group), an arylcarbonyl group (e.g., a phenylcarbonyl, tolylcarbonyl, etc., group), an alkoxycarbonyl group (e.g., a methoxycarbonyl, butoxycarbonyl, etc., group), an aryloxycarbonyl group (e.g., phenoxycarbonyl, tolyloxycarbonyl, etc., group), a sulfo group, an acyloxy group (e.g., an acetyl group, etc.), a sulfamoyl group (e.g., a N-methylsulfamoyl, N,N-diethylsulfamoyl, N-methyl-N-phenylsulfamoyl, etc., group), a carbamoyl group (e.g., an N-ethylcarbamoyl, N-methyl-N-decylcarbamoyl, N-phenylcarbamoyl, etc., group), an acylamino group (e.g., an acetamido, butyramido, benzamido, etc., group), a diacylamino group (e.g., a phthalimido, 3-heptadecylsuccinimido, etc., group), a ureido group (e.g., an ethylureido, phenylureiod, chlorophenylureido, etc., group), a thioureido group (e.g., an ethylthioureido, phenylthioureido, chlorphenylthioureido, etc., group), an alkoxycarbonylamino group (e.g., a methoxycarbonylamino, octoxycarbonylamino, etc., group), an aryloxycarbonylamino group (e.g., a phenoxycarbonylamino group, etc.), an alkoxythiocarbonylamino group (e.g., a methoxythiocarbonylamino, octoxythiocarbonylamino etc., group), an aryloxythiocarbonylamino group (e.g., a phenoxythiocarbonylamino group, etc.), a sulfonamido group (such as an alkylsulfonamido (e.g., methylsulfonamido, ethylsulfonamido, etc.), arylsulfonamido (e.g., phenylsulfonamido, etc.), etc. group), a heterocyclic group (e.g, a 5- or 6-membered heterocyclic group or condensed hetocyclic group containing at least one hereto atom selected from nitrogen, oxygen and sulfur atoms, such as a furyl, oxazolyl, benzothiazolyl, imidazolyl, etc., group), an arylsulfonyloxy group (e.g., a phenylsulfonyloxy, tolylsulfonyloxy, etc., group), an alkylsulfonyloxy group (e.g., an ethylsulfonyloxy, dedecylsulfonyloxy, etc., group), an arylsulfonyl group (e.g., a phenylsulfonyl, tolylsulfonyl, etc., group), an alkylsulfonyl group (e.g., a methylsulfonyl, octylsulfonyl, etc., group), an arylthio group (e.g, a phenylthio, tolylthio, etc., group), an alkylthio group (e.g., a methylthio, octylthio, dodecylthio, etc., group), an alkylsulfinyl group (e.g., a methylsulfinyl, hexylsulfinyl, etc., group), an arylsufinyl group (e.g., a phenylsulfinyl, tolysulfinyl, etc., group), an alkylamino group (e.g., a methylamino, butylamino, etc., group), an dialkylamino group (e.g., an N,N-diethylamino, N-methyl-N-decylamino, etc., group), an anilino group (such as an N-alkylanilino (e.g., N-methylanilino, etc.), .N-arylanilino (e.g., N-phenylanilino, etc.), N-acylanilino (e.g., 2-chloro-5-tetradecanamidoanilino, etc.), etc., group), a hydroxyl group, or a mercapto group.

Furthermore W represents an aryl group (e.g., a phenyl or an α-or β-naphthyl group) or an aryl group having one or more substituents such as an alkyl group (e.g., a methyl, ethyl, octyl, etc., group), an alkenyl group (e.g., an allyl, β-vinylethyl, etc., group), a cycloalkyl group (e.g., a cyclohexyl, norbornyl, 7,7-dialkylnorbonyl, 2-pentadecyl-7,7-dialkylnorbornyl, etc., group), an aralkyl group (e.g., a benzyl, β-phenylethyl, etc., group), an cycloalkenyl group (e.g., a cyclopentenyl, cyclohexenyl, etc., group), a halogen atom (e.g., a chlorine, bromine, fluorine, etc., atom), a nitro group, a cyano group, an aryl group (e.g., a phenyl, tolyl, ethoxyphenyl, naphthyl, etc., group), an alkoxy group (e.g., a methoxy, butoxy, octyloxy, etc., group), an aryloxy group (e.g., a phenoxy, tolyloxy, naphthoxy, etc., group), a carboxy group, an alkylcarbonyl group (e.g., a methylcarbonyl, octylcarbonyl, etc., group), an arylcarbonyl group (e.g., a phenylcarbonyl, tolylcarbonyl, etc., group), an alkoxycarbonyl group (e.g., a methoxycarbonyl, butoxycarbonyl, etc., group), an aryloxycarbonyl group (e.g., a phenoxycarbonyl, tolyloxycarbonyl, etc., group), a sulfo group, an acyloxy group (e.g., an acetoxy, etc., group), a sulfamoyl group (e.g., a methylsulfamoyl, diethylsulfamoyl, phenylsulfamoyl, etc., group), a carbamoyl group (e.g., a carbamoyl, N-octadecylcarbamoyl, N,N-dihexylcarbamoyl, N-methyl-N-phenylcarbamoyl, 3-pentadecylphenylcarbamoyl, etc., group), an acylamino group (e.g., an acetamido, butyramido, benzamido, etc., group), a diacylamino group (e.g., a succinimido, phthalimido, hydantoinyl, etc., group), a ureido group (e.g., an ethylureiod, phenylureido, chlorophenylureido, etc., group), a thioureido group (e.g., an ethylthioureido, phenylthioureido, chlorphenylthiouredio, etc., group), an alkyloxycarbonylamino group (e.g., a methoxycarbonylamino, octoxycarbonylamino, etc., group), an aryloxycarbonylamino group (e.g., a phenyloxycarbonylamino etc., group), an alkoxythiocarbonylamino group (e.g., a methoxythiocarbonylamino, octoxythiocarbonylamino, etc., group), an aryloxythiocarbonylamino group (e.g., a phenoxythiocarbonylamino group, etc.), a sulfonamido group (such as an alkylsulfonamido (e.g, methylsulfonamido, ethylsulfonamido, etc.), arylsulfonamido (e.g., phenylsulfonamido, etc.), etc., group), a heterocyclic group (e.g., a 5- or 6- membered heterocyclic group of condensed heterocyclic group containing at least one hetero atom selected from nitrogen, oxygen and sulfur atoms, such as a furyl, oxazolyl, benzothiazolyl, imidazolyl, etc., group), an arylsulfonyloxy group, (e.g., a phenylsulfonyloxy, tolysulfonyloxy, etc., group), an alkylsulfonyloxy group, (e.g., an ethylsulfonyloxy, dodecylsulfonyloxy, etc., group), an arylsufonyl group, (e.g., a phenylsulfonyl, tolysulfonyl, etc., group), an alkylsulfonyl group (e.g., a methylsulfonyl, octylsulfonyl, etc., group), an alrylthio group (e.g., phenylthio, tolythio, etc., group), an alkylthio group, (e.g., a methylthio, octylthio, dodecylthio, etc., group), an alkylsulfinyl group, (e.g., a methlsulfinyl, hexysulfinyl, etc., group), an arylsulfinyl group, (e.g., a phenylsulfinyl, tolylsulfinyl, etc., group), an alkylamino group (e.g., a methylamino, butylamino, etc., group), a dialkylamino group, (e.g., an N,N-diethylamino, N-methyl-N-decylamino, etc., group), an anilino group, and N-alkylanilino group (e.g., an N-methylanilino group, etc.), an N-arylanilino group (e.g., an N-phenylanilino group, etc.), an N-acylanilino group (e.g., a 2-chloro-5-tetra-decanamidoanilino group), etc., a hydroxyl group, and a mercapto, group. More preferably W is a phenyl group substituted with an alkyl group, an alkoxy group, or a halogen atom in at least one of the orthio positions because in such case the coupler remaining in the photographic film processed causes less print out due to the action of heat and light.

Still further, W represents also a heterocyclic group (e.g., a 5-membered or 6-membered heterocyclic group containing a nitrogen atom (form example, a pyridyl, quinolyl or pyrrolyl group, substituted with a substituent as described above for the aryl group), or two or more nitrogen atoms (for example, a pyrazolyl, benzotriazolyl, tetrazolyl, etc., group), an oxygen atom (for example, an unsubstituted or substituted furyl or benzofuranyl group having a substituent described above for the aryl group); a sulfur atom (for example, an unsubstituted or substituted thienyl or benzo [b] thienyl group having a substituent as described above for the aryl group); and a heterocyclic group containing two or more different hetero-atoms (such as benzoazolyl, benzothiazolyl, and the like).

Moreover, W represents further an acyl group (such as an alkylcarbonyl group (e.g., an acetyl, butyryl, benzoyl, etc., group), a thioacyl group (such as an alkylthiocarbonyl group (e.g., an octylthiocarbonyl, etc., group), an alkylsulfonyl group (e.g., a methylsulfonyl, octylsulfonyl, etc., group), an arylsulfonyl group (e.g., a phenylsulfonyl, tolysulfonyl, etc., group)), an alkylsulfinyl group (e.g., a methylsulfinyl, hexylsulfinyl, etc., group), an arylsulfinyl group, (e.g., a phenylsulfinyl, tolylsulfinyl, etc., group), a carbamoyl group (such as an alkylcarbamoyl, dialkylcarbamoyl, arylcarbamoyl, etc., (e.g., N-ethylcarbamoyl, N-methyl-N-decylcarbamoyl, phenylcarbamoyl, etc.) group,) or a thiocarbamoyl group (such as an akylthiocarbamoyl (e.g., ethylthiocarbamoyl, etc.), dialkylthiocarbamoyl (e.g., N-methyl-N-decylthiocarbamoyl, etc.), arylthiocarbamoyl (e.g., phenylthiocarbamoyl, etc.), etc., group).

In the above described formulae, X represents a hydrogen atom, or has up to 40, preferably up to 22, carbon atoms. Suitable examples of groups for X include an alkyl group, an alkenyl group, a cycloalkyl group, an aralkyl group, or a cyloalkyenyl group are defined for W, and these groups may be substituted with one or more substituents as illustrated above in regard to the substituted alkyl group of W.

Furthermore, X represents also an aryl group as defined for W or a heterocyclic group as defined for W, each of which may also have one or more of the substituents as illustrated above for W.

Still further, X represents an alkoxycarbonyl group (e.g., a methoxycarbonyl, ethoxycarbonyl, stearyloxycarbonyl, etc. group), an aryloxycarbonyl group (e.g., a phenoxycarbonyl, α-naphthoxycarbonyl, β-naphthoxycarbonyl, etc. group), an aralkoxycarbonyl group (e.g., a benzyloxycarbonyl etc., group), an alkoxy group (e.g., a methoxy, ethoxy, decyloxy, etc., group), an aryloxy group (e.g. a phenoxy, tolyloxy etc., group), an alkylthio group (e.g., an ethylthio, dodecylthio, etc., group), an arylthio group (e.g., a phenylthio, α-naphthylthio, etc., group), a carboxy group, an acylamino group (e.g., an acetamido, 3-[(2,4-di-tert-amylphenoxy)acetamido]benzamido, etc., group), a diacylamino group (e.g., a phthalimido, 3-heptadecylsuccinimido, etc., group), an N-alkylacylamino group (e.g., an N-methylpropionamido, etc., group), an N-arylacylamino group (e.g., an N-phenylacetamido, etc., group), a ureido group (such as a ureido group, N-arylureido (e.g., N-phenylureido, etc.), N-alkylureido (e.g., an N-ethylureido group, etc.), etc., group), a thioureido group (such as a thioureido, N-arylthioureido (e.g., N-phenylthioureido, etc.), N-alkythioureido, (e.g., N-ethylthioureido, etc.), etc., group), an alkyloxycarbonylamino group, (e.g., a methoxycarbonylamino, octoxycarbonylamino, etc., group), an aryloxycarbonylamino group (e.g., a phenoxycarbonylamino group, etc.), an alkoxythiocarbonylamino group (e.g., a methyloxythiocarboxylamino, octoxythiocarbonylamino, etc., group), an aryloxythiocarbonylamino group (e.g., a phenoxythiocarbonylamino, etc., group), an anilino group (e.g., an N-phenylamino, 2-chloro-5-tetradecanamidoanilino, etc., group), an N-alkylanilino group (e.g., an N-methylanilino, etc., group), an N-arylanilino group (e.g., an N-phenylanilino, etc., group), an N-acylanilino group (e.g., an N-acetyl-(2-chloro-5-tetradecyloxycarbonyl)anilino, etc., group), an N-heterocyclic amino group (e.g., an N- oxazolylamino, N-thiazolylamino, etc., group), an N-alkyl-N-heterocyclic amino group (e.g., an N-methyl-N-oxazolylamino, etc., group), an N-aryl-N-heterocyclic amino group (e.g., an N-phenyl-N-pyridylamino, etc. group), an N-acylamino-N-heterocyclic amino group (e.g., an N-acetyl-N-benzimidazolylamino, etc. group), an N-alkylamino group (e.g., an N-butylamino, N-methylamino, etc., group), an N,N-dialkylamino group (e.g., an N,N-dibutylamino, etc, group), an N-cycloalkylamino group (e.g., an N-cyclohexylamino, etc., group), a cycloamino group (e.g., a piperidino, pyrrolidino, etc., group), an alkylcarbonyl group (e.g., a methylcarbonyl, etc., group), an arylcarbonyl group (e.g., a phenylcarbonyl, etc., group), a sulfonamido group (such as an alkkylsulfonamido (e.g., methylsulfonamido, etc.), arylsulfonamido (e.g., phenylsulfonamido, etc.), etc. group), a carbamoyl group (such as an N-alkylcarbamoyl group (e.g., N-methylcarbamoyl, N-{3-[(2,4-di-tert-amylphenoxy)acetamido]phenyl}carbamoyl, etc.), N,N-dialkylcarbamoyl (e.g., N-methyl-N-octadecylcarbamoyl, etc.), N-alkyl-N-arylcarbamoyl (e.g., an N-methyl-N-phenylcarbamoyl, etc.), N,N-diarylcarbamoyl (e.g., N,N-diphenylcarbamoyl, etc.), etc., group), a sulfamoyl group (such as an N-alkylsulfamoyl (e.g., N-methylsulfamoyl, N-{3-[(2,4-di-ter-tamylphenoxy)acetamido]phenyl}sulfamoyl, etc.), N,N-dialkylsulfamoyl (e.g., N-methyl-N-octadecylsulfamoyl, etc.), N-arylsulfamoyl group (e.g., N-phenylsulfamoyl, etc.), N-alkyl-N-arylsulfamoyl (e.g., a N-methyl-N-phenylsulfamoyl, etc.), N,N-diarylsulfamoyl (e.g., N,N-diphenylsulfamoyl, etc.), etc., group, a guanidino group (such as an N-alkylguanidino (e.g., N-methylguanidino, etc.), N-arylguanidino (e.g., N-phenylguanidino, etc.), etc., group) a cyano group, an acyloxy group (e.g., a tetradecanoyloxy, etc., group), a sulfonyloxy group (e.g., a benzenesulfonyloxy, etc., group), a hydroxyl group, a mercapto group, a halogen atom (e.g., a chlorine, bromine, fluorine, etc. atom), or a suflo group.

In the above-described formulae, T represents a hydrogen atom, or has up to 40, preferably up to 22, carbon atoms. Suitable examples of groups for T include a straight chain or branched chain alkyl group, an alkenyl group, a cycloalkyl group, an aralkyl group, or a cycloalkenyl group as defined for W, in which the groups may have one or more substituents as illustrated above in regard to the substituted alkyl group of W.

Furthermore T represents also an aryl group or a heterocyclic group, each as defined for W, in which each of these groups may have one or more substituents as described above in regard to W.

Still further, T represents a cyanol group, an alkoxy group (e.g., a methoxy, butoxy, octyloxy, etc., group), an aryloxy group (e.g., a phenoxy, tolyloxy, naphthoxy, etc., group), a halogen atom (e.g., a chlorine, bromine, fluorine, etc., atom), a carboxyl group, an alkoxycarbonyl group (e.g., a methoxycarbonyl, butoxycarbonyl, etc. group), an aryloxycarbonyl group, (e.g., a phenoxycarbonyl, tolyloxycarbonyl, etc., group), an acyloxy group (e.g., an acetoxy, etc., group), an alkylcarbonyl group (e.g., a methylcarbonyl, octylcarbonyl, etc., group), an arylcarbonyl group (e.g., a phenylcarbonyl, tolylcarbonyl, etc., group), a thioacyl group (such as an alkylthiocarbonyl group (e.g., an ethylthiocarbonyl etc., group) an arylthiocarbonyl group (e.g., a phenylthiocarbonyl, etc., group), a sulfo group, a sulfamoyl group (e.g., a methylsulfamoyl, diethylsulfamoyl, phenylsulfamoyl, etc., group), a carbamoyl group (such as an alkylcarbamoyl, dialkylcarbamoyl, arylcarbamoyl, etc., group, (e.g., N-ethylcarbamoyl, N-methyl-N-decylcarbamoyl, N-phenylcarbamoyl, etc., group), an acylamino group (e.g., an acetamido, butyramido, benzamido, etc., group), a diacylamino group (e.g., a phthalimido, 3-heptadecylsuccinimido, etc., group), a ureido group (e.g., an ethylureido, phenylureido, chlorophenylureido, etc., group), a thioureido group (e.g., an ethylthioureido, phenylthioureido, chlorophenylthioureido, etc., group), an alkoxycarbonylamino group (e.g., a methoxycarbonylamino, octoxycarbonylamino, etc., group), an aryloxycarbonylamino group (e.g., a phenoxycarbonylamino, etc., group), an alkoxythiocarbonylamino group (e.g., a methoxythiocarbonylamino, octoxythiocarbonylamino, etc., group), an aryloxthiocarbonylamino group (e.g., a phenoxythiocarbonylamino, etc., group), a sulfonamido group (such as an alkylsulfonamido (e.g., methylsulfonamido, ethylsulfonamido, etc.), arylsulfonamido (e.g., phenylsulfonamido, etc.), etc., group), an alkylsulfonyloxy group (e.g., an ethylsulfonyloxy, dodecylsulfonyloxy, etc., group), an arylsulfonyloxy group (e.g., a phenylsulfonyloxy, tolysulfonyloxy, etc., group), an arylsulfonyl group (e.g., a phenylsulfonyl, tolylsulfonyl, etc., group), an alkylsulfonyl group (e.g., a methylsulfonyl, octylsulfonyl, etc., group), an arylthio group (e.g., a phenylthio, tolylthio, etc., group), an alkylthio group (e.g., a methylthio, octylthio, dodecylthio, etc., group), an alkylsulfinyl group (e.g., a methylsulfinyl, hexylsulfinyl, etc., group), an arylsulfinyl group (e.g., a phenylsulfinyl, tolylsulfinyl, etc. group), an alkylamino group (e.g., a methylamino, butylamino, etc., group), a dialkylamino group (e.g., an N,N-diethylamino, N-methyl-N-decylamino, etc., group), an anilino group, an N-arylanilino group (e.g., an N-phenylanilino, etc., group), an N-alkylanilino group (e.g., an N-methylanilino, etc., group), an N-acylanilino group (e.g., a 2-chloro-5-tetradecanamidoanilino, etc., group), a hydroxyl group, or a mercapto group.

In the above-described general formulae, R has up to 40 carbon atoms and represents an alkyl group, an aryl group, or a heterocyclic group as defined for W.

Suitable examples of alkyl groups for R include a straight chain alkyl group, a branched chain alkyl group and an alkenyl group (such as a methyl, ethyl, isopropyl, allyl, hexenyl, pentadecyl, octadecyl, tert-butyl, etc., group), an aralkyl group (such as a benzyl, phenethyl, γ-phenylpropyl, etc., group), a cycloalkyl group (e.g., a cyclopentyl and a cyclohexyl, etc., group), and a cycloalkenyl group (e.g., a cyclopentenyl, cyclohexeneyl, etc., group). Each of these groups can be substituted with one or more substituents such as a halogen atom, a nitro group, a cyano group, an aryl group, an alkoxy group, an aryloxy group, a carboxyl group, an alkylcarbonyl group, an arylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, a heterocyclic group (e.g., a pyridyl group, a quinolyl group, a furyl group, a piperidyl group, etc.), an arylsulfonyl group, an alkylsulfonyl group, an arylsulfonyloxy group, an alkylsulfonyloxy group, and a substituted amino group (e.g., an N,N-diethylamino group, etc.), as defined for the substituents of the alkyl group of W.

Examples of aryl groups represented by R include a phenyl group, an α-naphthyl group, a β-naphthyl group, and a substituted aryl group, such as a substituted phenyl group, a substituted α-naphthyl group, and a substituted β-naphthyl group, in which these substituted aryl groups may have one or more substituents such as an alkyl group, an aralkyl group, an alkenyl group, a cycloalkyl group, a cycloalkenyl group, a halogen atom, a nitro group, a cyano group, an aryl group, an alkoxy group, an aryloxy group, a carboxyl group, an alkylcarbonyl group, an arylcarbonyl group, an alkoxycarbonyl group, an aryloxycarbonyl group, a sulfo group, an acyloxy group, a sulfamoyl group, an N,N-dialkylsulfamoyl group, an N-alkyl-N-arylsulfamoyl group, an N-alkylsulfamoyl group, an N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group (e.g., a pyridyl group, a quinolyl group, a furyl group, a piperidyl group, etc.), an alkylsulfonyl group, an arylsulfonyl group, and a substituted amino group (e.g., an N,N-dialkylamino group, an anilino roup, an N-acylanilino group, and an N-arylanilino group), as defined for the substituents of the aryl group of W.

Furthermore, the heterocyclic groups represented by R include a nitrogen-containing heterocyclic group (e.g., a pyridyl group, a quinolyl group, a pyrrolidyl group and a heterocyclic ring containing two or more nitrogen atoms such as a benzoimidazolyl group, and each of these groups or rings can have one or more substituents as illustrated above in regard to the aryl group of W), an oxygen-containing heterocyclic group (e.g., a tetrahydrofuryl group, a benzofuryl group, and each of these groups can have one or more substituents as illustrated above in regard to the aryl group of W, a sulfur-containing heterocyclic ring (e.g., a thienyl group, a benzothienyl group, and each of these groups can have one or more substituents as described above in regard to the aryl group of W), and a heterocyclic group having two or more different hetero atoms in the heterocyclic ring (e.g., a benzoxazolyl group, a benzothiazolyl group, etc.). $n$ represents 1 or 2 in the above general formulae (II) and (III).

The coupler represented by the general formula (II) and (III) of the present invention can combine directly at W, X, T or R or through a divalent group derived from W, X, T, or R to form a symmetrical or a symmetrical complex coupler, e.g., having the formula (IVa) to (IVd)

$$Cp—(W')_m—Cp \quad (IVa)$$

wherein W' represents a divalent moiety of the groups herein above described for W; and Cp represents a moeity of the general formula (IIa)

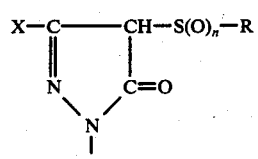
(IIa)

wherein X, R and $n$ are as hereinabove described; and $m$ is 0 or 1;

$$Cp—(X')_m—Cp \quad (IVb)$$

wherein X' represents a divalent moiety of the groups hereinabove described for X; and Cp, which may be the same or different, each represents a moiety of the formula (IIb) or (IIIa)

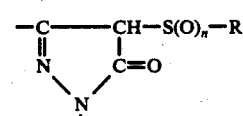
(IIb)

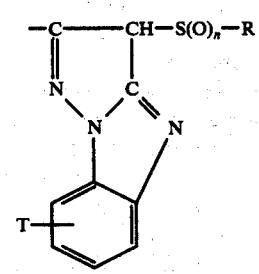
(IIIa)

wherein T, W, R and $n$ are as hereinabove defind; and $m$ is 0 or 1;

$$Cp—(T')_m—Cp \quad (IVc)$$

wherein T' represents a divalent moiety of the groups hereinabove defined for T; Cp represents a moiety of the formula (IIIb)

(IIIb)

wherein X, R and $n$ are as hereinabove defined; and $m$ is 0 or 1; and $$Cp—(R')_m—Cp \quad (IVd)$$

wherein R' represents a divalent moiety of the groups hereinabove defined for R; and Cp, which may be the same or different, each represents a moiety of the formula (IIc) or (IIIc)

(IIc)

(IIIc)

-continued

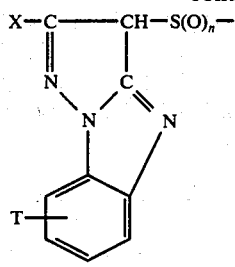

wherein T, W, X and n are as hereinabove defined; and m is 0 or 1.

The magenta coupler used in the present invention has various properties depending on the substituents of W, X, T and R and this feature is suitable for use to achieve various photographic objects. When at least one of W, X, T and R contains a hydrophobic group containing 8 or more carbon atoms, the coupler associates in a hydrophilic colloid and becomes non-diffusible in the hydrophilic colloid layer of a light-sensitive material. Such a coupler can be incorporated in a silver halide emulsion layer. A coupler which does not have a diffusion resistant hydrophobic group in the coupler molecule is added to a developer solution and forms insoluble dye in a light-sensitive layer during color development. When R contains a diffusion-resistant hydrophobic group and at least one of W, X and T contains a water-solubilizing group, such as a sulfo group or a carboxy group, the coupler per se is non-diffusible but provides a diffusible dye by the oxidizing coupling reaction with an aromatic primary amine developing agent. Such a diffusible dye providing coupler is suitable for use in diffusion transfer color photography, although this coupler can be used in a conventional color photographic light-sensitive material as well.

The coupler used in a silver halide photographic emulsion layer, i.e., the so-called incorporated type coupler must be fixed in the emulsion layer, that is, must be diffusion-resistant. If the coupler is not diffusion-resistant, the coupler migrates in the light-sensitive material and the dye is formed in the wrong light-sensitive emulsion layer, thus markedly deteriorating the color reproduction capability of the light-sensitive material.

In order to render a coupler diffusion-resistant, a group containing a hydrophobic residue of 8 to 32 carbon atoms is introduced into the coupler molecule. This residue is generally called a "ballast group". The ballast group can be combined with the coupler skeleton directly or through an imino bond, an ether bond, a carbonamido bond, a sulfonamido bond, an ureido bond, an ester bond, an imido bond, a carbamoyl bond, a sulfamoyl bond, and the like.

Some examples of the ballast groups are shown in the specific examples of couplers according to the present invention set forth hereinafter.

Specific examples of the ballast groups which can be used are as follows.

I. Alkyl groups and alkenyl groups
For example, $-CH_2-CH(C_2H_5)_2, -C_{12}H_{25}-, -C_{16}H_{33}, -C_{17}H_{33}$ II. Alkoxyalkyl groups
For example, $-(CH_2)_3-O-(CH_2)_7CH_3$,

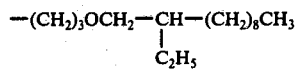

as described in Japanese Patent Publication No. 27563/1964.

III. Alkylaryl groups
For example,

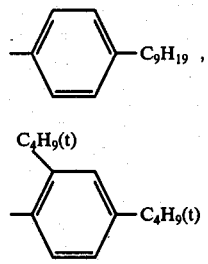

IV. Alkylaryloxyalkyl groups
For example,

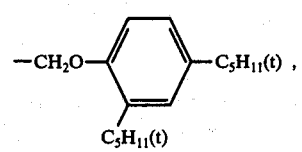

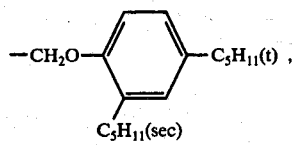

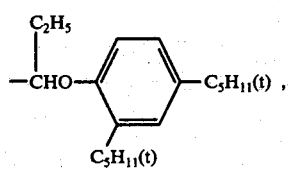

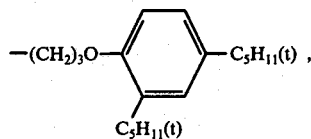

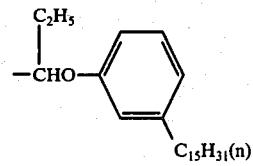

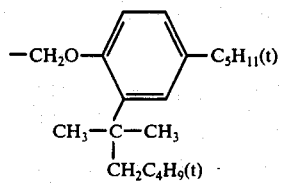

-continued

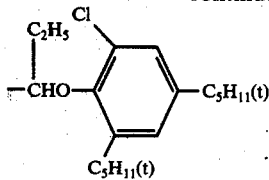

V. Acylamidoalkyl groups
For example,

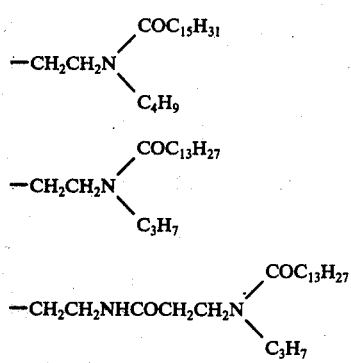

as described in U.S. Pat. Nos. 3,337,344 and 3,418,129.

VI. Alkoxyaryl groups and aryloxyaryl groups
For example,

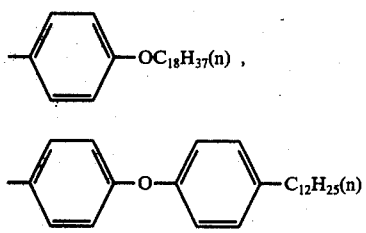

VII. Residues having both a long chain aliphatic group such as an alkyl group or an alkenyl group and a water-solubilizing group such as a carboxy group or a sulfo group
For example,

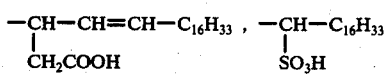

VIII. Alkyl groups substituted with an ester group
For example,

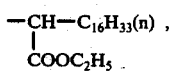

IX. Alkyl groups substituted with an aryl group or a heterocyclic group
For example,

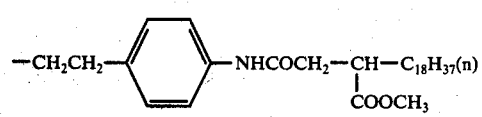

-continued

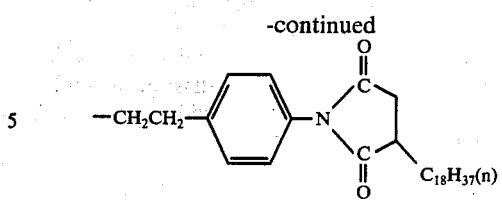

X. Aryl groups substituted with an aryloxyalkoxycarbonyl group
For example,

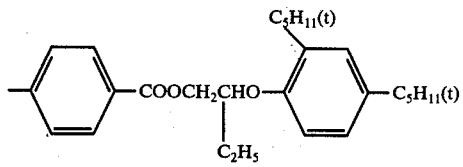

A coupler dispersion of the coupler of the present invention can be advantageously prepared by dissolving the coupler into either an organic solvent which has a high boiling point, e.g., higher than about 170° ) and is immiscible with water, a low boiling organic solvent and a water-soluble organic solvent or a high boiling water-immiscible organic solvent and/or a low boiling organic solvent and/or a water-soluble organic solvent.

The high boiling water-immiscible organic solvents described in U.S. Pat. No. 2,322,027 can used as a solvent. Examples of preferred solvents are di-n-butyl phthalate, benzyl phthalate, triphenyl phosphate, tri-o-cresyl phosphate, diphenyl mono-o-chlorophenyl phosphate, monophenyl di-o-chlorophenyl phosphate, dioctyl phthalate, dibutyl sebacate, acetyltributyl citrate, tri-tert-octyl trimelitate, n-nonyl-phenol, dioctyl butyl phosphate, N,N-diethyl laurylamide, 3-pentadecylphenyl ethyl ether, 2,5-di-sec-amylphenyl butyl ether, and the like.

Low boiling (e.g., boiling at lower than about 170° C) or water-soluble organic solvents which can be used together with or in place of the high boiling solvent are described in U.S. Pat. Nos. 2,801,171; 2,801,170; 2,949,360; etc. Examples of these organic solvents are as follows.

1. Organic solvents which have a low boiling point and are substantially insoluble in water such as methyl acetate, ethyl acetate, propyl acetate, butyl acetate, isopropyl acetate, ethyl propionate, secondary butyl alcohol, ethyl formate, butyl formate, nitromethane, nitroethane, carbon tetrachloride, chloroform, and the like.

2. Water-soluble organic solvents such as methyl isobutyl ketone, β-ethoxyethylacetate, Carbitol acetate (diethyleneglycol monoacetate), methoxytriglycol acetate, acetyl acetone, diacetonealcohol, butyl Carbitol, methyl Carbitol, methyl ethyl ketone, methanol, ethanol, acetonitrile, dimethylformamide, dioxane, and the like. It is desirable for the solvent to have a sufficiently low water content so as to not adversely affect the solubility of the coupler in the solvent.

The low boiling or water-soluble solvent can be removed from a coupler dispersion by air-drying the cooled noodle-like dispersion or washing the cooled noodle-like dispersion continuously with water such as described in U.S. Pat. No. 2,801,171.

For the dispersion of an oil-soluble coupler, an emulsifying homogenizer, a colloid mill, an ultrasonic wave emulsifying apparatus, and the like are suitable. A diffusion resistant coupler having both a ballast group and a carboxylic acid group or a sulfonic acid group in the molecule is soluble in a neutral or weakly alkaline aqueous solution. This coupler can be incorporated in a photograhic emulsion by adding such an aqueous solution containing the coupler to the photograhic emulsion. The coupler is believed to be diffusion resistant through the formation of miscelles in the hydrophilic polymer.

Specific examples of couplers according to the present invention are set forth below, but the present invention is not to be construed as being limited to only these couplers.

Coupler 1
1-(2,4,6-Trichlorophenyl)-3-{3-[(2,4-di-tert-pentylphenoxy)-acetamido]benzamido}-4-phenylsulfonyl-5-oxo-2-pyrazoline Coupler 2
1-(2,4,6-Trichlorophenyl)-3-{3-[α-(3-tert-butyl-4-hydroxyphenoxy)tetradecanamido]benzamido}-4-tetradecylsulfonyl-5-oxo-2-pyrazoline Coupler 3
2-Heptadecyl-3-(3-ethoxycarbonylphenylsulfonyl)-3H-pyrazolo-[1,5-a]-benzimidazole Coupler 4
1-(2,4,6-Trichlorophenyl)-3-methoxy-4-(2-ethoxycarbonylphenylsulfonyl)-5-oxo-2-pyrazoline Coupler 5
1-(2-Chloro-4,6-dimethylphenyl)-3-{2-chloro-4-[γ-(2,4-di-tert-pentylphenoxy)propylsulfamoyl]anilino}-4-(3-nitrophenylsulfonyl-5-oxo-2-pyraxoline Coupler 6
1-(2,4,6-Trichlorophenyl)-3-[(3-n-octadecylsuccinimido)-benzamido]-4-phenylsulfinyl-5-oxo-2-pyrazoline Coupler 7
1-(2,6-Dichloro-4-methoxyphenyl)-3-{3-[α-(2,4-di-tert-pentylphenoxy)butyramido]benzamido}-4-tetradecylsulfonyl-5-oxo-2-pyrazoline Coupler 8
1-(2,4,6-Trichlorophenyl)-3-(3,5-dicarboxyanilino)-4-(3-octadecylcarbamoylphenylsulfonyl)-5-oxo-2-pyrazoline Coupler 9
2-[3-(α-Octyloxymethylpropylamido)benzamido]-3-phenylsulfinyl-7-chloro-3H-pyrazolo-[1,5-a]-benzimidazle Coupler 10
1-(3-Sulfo-4-phenoxyphenyl)-3-n-octadecyl-4-phenylsulfonyl 5-oxo-2-pyrazoline Coupler 11
1-(2,4,6-Trichlorophenyl)-3-{3-[α-(2,4-di-tert-pentylphenoxy)butyramido]benzamido}-4-dodecylsulfonyl-5-oxo-2-pyrazoline Coupler 12
1-(2,4,6-Trichlorophenyl)-3-[(2-chloro-5-tetradecanamido)-anilino]-4-(3-acetylaminophenylsulfonyl)-5-oxo-2-pyrazoline Coupler 13
1-{4-[(2,4-Di-tert-pentylphenoxy) acetamido]-phenyl}-3-(2,4-dichloroanilino)-4-phenylsulfonyl-5-oxo-2-pyrazoline Coupler 14
1-(2,4,6-Trichlorophenyl)-3-{3-[α-(2,4-di-tert-pentylphenoxy)butyramido]phenylureido}4-(2-pyridylsulfonyl)-5-oxo-2-pyrazoline Coupler 15
1-(2,4,6-Trichlorophenyl)-3-[2-chloro-5-(2-carboxymethyl-2-nonadecenylamido)anilino]-4-(1-naphthylsulfonyl)-5-oxo-2-pyrazoline Coupler 16
1-(2,6-Dichloro-4-methoxyphenyl)-3-{3-[α-(2,4-di-tert-pentylphenoxy)butyramido]benzamido}-4-(2-ethoxycarbonylphenylsulfonyl)-5-oxo-2-pyrazoline The magenta couplers of the present invention can be easily prepared, in general, by oxidizing magenta couplers having a monothio group at the coupling position with an appropriate oxidizing agent. The magenta couplers having a monothio group at the coupling position used as starting materials in the oxidation can be prepared by reacting four-equivalent magenta couplers with various kinds of sulfenyl chlorides in an inert solvent such as carbon tetrachloride, chloroform, etc., according to the method described in, for example, U.S. Pat. No. 3,227,554. The thus obtained magenta couplers are oxidized under appropriate conditions readily convert the monothio group attached to the coupling position of the coupler to a sulfinyl group or a sulfonyl group. The oxidation reaction can be carried out using an appropriate oxidizing agent (for example, hydrogen peroxide, perbenzoic acid, manganese dioxide, sodium metaperiodate, etc., preferably hydrogen peroxide, sodium metaperiodate and maganese dioxide) in a solvent which is inert to the oxidation reaction (for example, water, acetic acid, ethanol, chloroform, etc.) at a temperature of about −10° to 100° C. A suitable molar ratio of the oxidizing agent to the thio group containing coupler can range from about 1:1 to about 1:1.2 and from about 1:2 to about 1:4 to obtain an —SO— group and an —$SO_2$— group in the coupler, respectively. In a preferred embodiment, the reaction is conducted in acetic acid at a temperature of 20° to 70° C using hydrogen peroxide to provide the desired compound.

Typical examples of the synthesis of the couplers of the present invention are illustrated below. Unless otherwise indicated herein, all parts, percentages, ratios and the like are by weight.

SYNTHESIS EXAMPLE 1

Preparation of 1-(2,4,6-Trichlorophenyl)-3-methoxy-4-(2-ethoxycarbonylphenylsulfonyl)-5-oxo-2-pyrazoline (Coupler 4)

1.0 g of 1-(2,4,6-Trichlorophenyl)-3-methoxy-42-ethoxycarbonylphenylthio)-5-oxo-2-pyrazoline, which was prepared by the method described in U.S. Pat. No. 3,227,554, was dissolved in 20 ml of acetic acid and 0.8 g of a 35% aqueous hydrogen peroxide solution was added thereto with stirring and maintaining the reaction temperature at 50° C. The reaction mixture was heterogeneous initially but became homogeneous as the reaction proceeded. After reaction for five hours at the above described temperature, the reaction mixture was poured into 100 ml of a saturated aqueous sodium chloride solution and the solid deposited was collected by filtration. By recrystallization from 10 ml of methanol, 0.8 g of Coupler 4 having a melting point of 185° to 187° C was obtained.

Elemental Analysis: Calculated for $C_{19}H_{15}N_2O_6SCl_3$ (%): C; 45.24; H; 2.98; N; 5.56. Found (%): C; 45.21; H; 3.16; N; 5.79.

SYNTHESIS EXAMPLE 2

Preparation of
1-(2,4,6-Trichlorophenyl)-3-{3-[α(2,4-di-tert-pentyl-phenoxy)butyramido]benzamido}-4-dodecylsulfonyl-5-oxo-2-pyrazoline (Coupler 11)

7.3 g of 1-(2,4,6-trichlorophenyl)-3-{3-[α-2,4-di-tert-pentylphenoxy)butyramido]benzamido}-4-dodecylthio-5-oxo-2-pyrazoline, which was prepared by the method described in U.S. Pat. No. 3,227,554, was dissolved in 50 ml of acetic acid and 2.0 g of a 35% aqueous hydrogen peroxide solution was added dropwise thereto at room temperature (i.e., 20°–30° C) with stirring. The reaction mixture became clear as the reaction proceeded. After reaction for 2 hours, the reaction mixture was poured into 200 ml of a saturated aqueous sodium chloride solution and the solid deposited was collected by filtration. By recrystallization from 50 ml of acetonitrile, 6.2 g of Coupler 11 having a melting point of 88.5° to 90° C was obtained.

Elemental Analysis: Calculated for $C_{48}H_{65}N_4O_6SCl_3$ (%): C; 61.94; H; 6.99; N; 6.02. Found (%): C; 61.94; H; 7.02; N; 6.26.

The couplers of the present invention can be clearly distinguished from conventionally known two-equivalent magenta couplers in their chemical structures, although they are obtained by oxidation of known thio-substituted two-equivalent couplers.

The sulfinic acids which are formed upon coupling during color development are particularly useful for improving the properties of photographic materials due to their anti-fogging effects on the photographic emulsion and graininess improving effects, as described in P. Glafkides, *Photographic Chemistry*, Vol. I, Page 378, Fountain Press, London (1958). Further, the effects of the split-off group on a photographic emulsion are mild in comparison with those of thio-substituted type split-off groups and the couplers of the present invention have excellent properties in that they are convenient in practical use. Furthermore, the couplers of the present invention can be easily prepared.

The coupler of the present invention has the useful property in that is is stable in a photographic emulsion layer during storage and, in particular, the decrease in coupling reactivity during storage under at low temperatures or high humidities is less in comparison with another known two-eqivalent couplers. The stability of an unexposed photographic light-sensitive material is one of the important factors in assessing the characteristics of a color photographic light-sensitive material.

The color images obtained from the coupler of the present invention are much more stable to heat than other two-equivalent couplers and four-equivalent couplers whose coupling position is unsubstituted.

The coupler of the present invention can be converted into an azomethine dye in a high yield by the oxidizing coupling reaction using an exposed silver halide as an oxidizing agent. Some of the four-equivalent couplers used in the prior art have a low conversion yield into the dye, since the leuco dye as an intermediate product produces side reactions such as azine ring formation. On the contrary, the coupler of the present invention can be converted into an azomethine dye in a high yield, since the reaction does not proceed through such a reactive intermediate product. Consequently, in the photographic light-sensitive material using the coupler of the present invention, it is possible to reduce the quantity of the magenta forming coupler, to reduce the content of the silver halide and to reduce the thickness of the emulsion layer. Thus, it is easy to reduce the cost of the light-sensitive material, to improve the sharpness and to promote the development.

The coupler of the present invention has a strong coupling activity for an oxidized aromatic primary amine color developing agent and rapidly removes the oxidized product of the developing agent formed during color development, so that the development of a silver halide emulsion is accelerated.

In the coupler of the present invention, the process of forming a dye is completed in a color developing bath and it is not necessary to use thereafter a bleaching bath containing a strong oxidizing agent such as potassium ferricyanide or potassium bichromate. Thus a treatment with a blixing bath containing a silver complex salt forming agent and a weak oxidizing agent such as a ferric chelate of ethylenediamine tetraacetic acid (EDTA) or a bleaching bath containing a ferric salt (for example, ferric chloride) is possible and, consequently, it is easy to shorten the overall time for the color processings as well as to solve the problem of environmental pollution in processing solution discharge.

The coupler of the present invention is inactivated by carbonyl compounds such as aldehydes and ketones to a lesser extent, while the coupling-position unsubstituting magenta coupler used in the prior art, in particular, in an emulsion layer is changed into a compound having low color forming reactivity such as a methylol or methelene-bis-compound by formaldehyde in the air, which often does not provide sufficient color formation during color development. One feature of the color photographic light-sensitive material according to the present invention is that the material is hardly influenced by such chemicals.

The coupler of the present invention has the advantages when used for conventional color photographic light-sensitive materials, as described in the Examples set forth hereinafter, that the stability during the passage of time is high in an emulsion layer and, in particular, the reduction in color formation even after the passage of time at low temperature or under high humidity is less, as compared with other known two-equivalent couplers. In a color photographic light-sensitive material, the stability of the duration of a fresh film is one of the most important factors as to the assessment of the characteristics thereof as set forth hereinbefore.

Moreover, it has been found that a color developed dye image formed from the magenta coupler of the present invention has superior heat resistance to the color developed dye image formed from coupling-position unsubstituted couplers and, even in comparison with the foregoing known couplers having a 4-position substituent on the same pyrazolone nucleus, the coupler of the present invention has a higher heat resistance.

The two-equivalent magenta coupler of this invention can be used together with other magenta couplers as described in, for instance, U.S. Pat. Nos. 2,439,089; 2,369,489; 2,600,788; 3,558,319; 2,311,081; 3,419,391; 3,214,437; 3,006,759; 2,725,292; 3,408,194; 2,908,573; 3,519,429; 3,615,506; 3,432,521; 3,152,896; 3,062,653; 3,582,322; 2,801,171; 3,311,476; British Pat. No. 956,261; Japanese Patent Publication Nos. 2016/1969 and 19032/1971; Japanese Patent Application Nos. 114445/1972; 56050/1973; 45971/1973; 21454/1973; 108798/1973; and 114446/1972, in which the amount of these other magenta couplers employed with the two equivalent magenta couplers of the invention, in general, ranges from about 5 to 80 mole % based on the total amount of the magenta couplers employed, with the magenta couplers as described in U.S. Pat. Nos. 2,983,608; 2,455,170; 2,725,292; 3,005,712; 3,519,429; and 2,688,539; British Pat. Nos. 800,262 and 1,044,778; and Belgian Pat. No. 676,691, in which these magenta-colored couplers can be incorporated in an amount from about 2 to 20 mole % to the total amount of the magenta couplers employed; with the so-called development inhibitor releasing type couplers capable of imagewise releasing development inhibiting compounds at development such as, for instance, the monothio type couplers as described in U.S. Pat. Nos. 3,227,550 and 3,227,554 and British Pat. No. 953,454, the o-aminophenylazo type couplers as described in U.S. Pat. No. 3,148,062, and the couplers as described in Japanese Patent Publication No. 8750/1972 and German Patent Application (OLS) No. 2,163,811, with these couplers generally being incorporated in an amount from about 2 to 20 mole % to the total amount of the magenta couplers employed; and also with the hydroquinone releasing development inhibiting compounds as described in U.S. Pat. No. 3,297,445 and British Pat. No. 1,058,606, in which these hydroquinone releasing compounds can be employed therewith in an amount from about 2 to 20 mole % to the total amount of the magenta couplers employed.

Two or more of the above described compounds such as magenta couplers and the like can be incorporated in the same layer or the couplers and the like can be incorporated in two or more layers, in order to achieve the characteristics required in a photographic light-sensitive material. In general, the coupler of the present invention can be coated on a support in an amount ranging from about $1 \times 10^{-4}$ to $5 \times 10^{-3}$ mole/m$^2$, preferably $3 \times 10^{-4}$ to $2 \times 10^{-3}$ mole/m$^2$.

The coupler of the present invention can also be used in a developer solution. In such case a suitable amount of the coupler ranges from about 0.2 to 50 g, preferably 0.5 to 10 g, per liter of the developer solution.

The coupler of the present invention is advantageously used in combination with a green-sensitive silver halide emulsion.

To improve the fastness to light of the magenta dye formed in an emulsion layer or an adjacent layer thereof, or to prevent yellowing or print-out of the coupler remaining in an unexposed portion of color stain, the photographic light-sensitive material used in the present invention advantageously contains a p-substituted phenol derivative. Particularly suitable p-substituted phenol derivatives can be selected from the hydroquinone derivatives described in U.S. Pat. Nos. 2,360,290; 2,418,613; 2,675,314; 2,701,197; 2,704,713; 2,710,801; 2,728,659; 2,732,300; 2,735,765 and 2,816,028, the gallic acid derivatives described in U.S. Pat. Nos. 3,457,079 and 3,069,262 and Japanese Patent Publication No. 13496/1968, the p-alkoxyphenols described in U.S. Pat. No. 2,735,765 and Japanese Patent Application (OPI) No. 4738/1972 and the p-oxyphenol derivatives described in U.S. Pat. Nos. 3,432,300; 3,573,050; 3,574,627; 3,764,337 and 3,698,909 and Japanese Patent Publication No. 20977/1974.

Silver halide emulsions are usually prepared by mixing a solution of a water-soluble silver salt, for example, silver nitrate with a water-soluble halide, for example, potassium bromide in the presence of a water-soluble polymer, for example, gelatin. In addition to silver chloride and silver-bromide, mixed silver halides such as silver chlorobromide, silver iodobromide and silver chloroiodobromide can be employed in the present invention. The silver halide grains can be prepared according to conventional methods, including the so-called single jet method, double jet method and controlled double jet method. A mixture of two or more silver halide photographic emulsions which are prepared separatedly can also be used. The silver halide grains can have a homogeneous crystal structure, a layered structure in which the interior differs from the outer layer, or the so-called conversion-type silver halide grains as described in British Pat. No. 635,841 and U.S. Pat. No. 3,622,318. Silver halide grains which form a latent image predominantely on the surface of the grains or predominantly in the interior of the grains can also be used. These photographic emulsion can be prepared using various known methods such as an ammonia method, a neutral method and an acid method.

The silver halide emuslion described above can be chemically sensitized using conventional methods. Specific examples of suitable chemical sensitizers include, for example, gold compounds such as chloroaurates and gold trichloride as described in U.S. Pat. Nos. 2,399,083; 2,540,085; 2,579,856 and 2,597,915; salts of a noble metal, such as platinum, palladium, irridium, rhodium and ruthenium, as described in U.S. Pat. Nos. 2,448,060; 2,540,086; 2,566,245; 2,566,263 and 2,598,079; sulfur compounds capable of forming silver sulfide by reacting with a silver salt, such as those described in U.S. Pat. Nos. 1,574,944; 2,410,689; 3,189,458 and 3,501,313; stannous salts, amines, and other reducing compounds such as those described in U.S. Pat. Nos. 2,487,850; 2,518,698; 2,521,925; 2,521,926; 2,694,637; 2,983,610 and 3,210,254, and the like.

Examples of the hydrophilic colloids which can be used as a vehicle for the silver halide grains includes, for example, gelatin, colloidal albumin, casein, a cellulose derivative such as carboxymethylcellulose and hydroxyethylcellulose, agar, sodium alginate, a starch derivative, a synthetic hydrophilic colloid such as polyvinylalcohol, poly-N-vinylpyrrolidone, a polyacrylic acid copolymer and polyacrylamide, or the derivatives or partially hydrolyzed products thereof. If desired, a compatible mixture of these colloids can also be used. Of these colloids, gelatin is most commonly employed. The gelatin can be replaced partially or completely by a synthetic polymer, by a so-called gelatin derivative such as those prepared by reacting or modifying the amino, imino, hydroxy carboxy groups contained, as functional groups, in the gelatin molecule with a compound having a group capable of reacting with the above described groups, or a graft gelatin such as those prepared by grafting another polymer chain on the gelatin molecule.

The photgraphic emulsion can be spectrally sensitized or super-sensitized, if desired, using a cyanine dye such as cyanine, merocyanine, carbocyanine or styryl dyes, individually or in combination. These spectral sensitization techniques are well known, and are described, for example, in U.S. Pat. Nos. 2,688,545; 2,912,329; 3,397,060; 3,615,635 and 3,628,964, British Pat. Nos. 1,195,302; 1,242,588 and 1,293,862, German Patent Application (OLS) Nos. 2,030,326 and 2,121,780 and Japanese Patent Publication Nos. 4936/1968 and 14030/1969. The sensitizers can be chosen as desired depending on the spectral range, sensitivity, and the like depending on the purpose and end-uses of the photographic materials to be sensitized.

Various kinds of conventional stabilizers or anti-fogging agent can be added to the photographic emulsion described above in order to prevent a reduction in the sensitivity or a formation of fog during preparation, storage or processing. A wide variety of such compounds are known such as heterocyclic compounds, mercury-containing compounds, mercapto compounds or metal salts, including 4-hydroxy-6-methyl-1,3,3a,7-tetrazaindene, 3-methylbenzothioazole and 1-phenyl-5-mercaptotetrazole.

The photographic emulsion can be hardened using conventional methods. Examples of suitable hardeners include, for example, aldehyde type compounds such as formaldehyde and glutaraldehyde; ketone compounds such as diacetyl and cyclopentanedione; reactive halogen-containing compounds such as bis(2-chloroethylurea), 2-hydroxy-4,6-dichloro-1,3,5-triazine and those described in U.S. Pat. Nos. 3,288,775 and 2,732,313 and British Pat. Nos. 974,723 and 1,167,207; divinylsulfone; 5-acetyl-1,3-diacryloyl-hexahydro-1,3,5-triazine; the compounds described in U.S. Pat. Nos. 3,635,718 and 3,232,763, British Pat. No. 994,869, U.S. Pat. Nos. 2,732,316; 2,586,168; 3,103,437; 3,017,280; 2,983,611; 2,725,294; 2,725,295; 3,100,704; 3,091,537; 3,321,313; 3,543,292; etc.

The photographic emulsion described above can also contain one or more surface active agents. These surface active agents are used as a coating aid, a dispersing agent, a sensitizer, an agent for improving the photographic properties, an antistatic agent or an adhesion preventing agent. Suitable surface active agents include natural surface active agents such as saponin; nonionic surface active agents such as alkylene oxides, glycerols and glycidols; cationic surface active agents such as higher alkylamines, quaternary ammonium salts, heterocyclic compounds such as pyridine and the like, phosphoniums or sulfoniums; anionic surface active agents containging an acid group such as a carboxylic acid group, a sulfonic acid group, a phosphoric acid group, a sulfuric acid ester group or a phosphoric acid ester group; amphoteric surface active agents such as amino acids, aminosulfonic acids, aminoalcohol sulfuric acid esters or aminoalcohol phosphoric acid esters. Some examples of surface active agents which can be used are described, for example, in U.S. Pat. Nos. 2,271,623; 2,240,472; 2,288,226; 2,739,891; 3,068,101; 3,158,484, 3,201,253; 3,210,191; 3,294,540; 3,415,649; 3,441,413, 3,442,654, 3,475,174 and 3,545,947, German Patent Application (OLS) No. 1,942,665, British Pat. Nos. 1,077,317 and 1,198,450, and the like.

The magenta coupler of the present invention can be used in a multilayer color photographic light-sensitive material containing a yellow coupler and a cyan coupler. An open-chain diketomethylene type compound is conventionally used as a yellow coupler. Examples of such compounds are described, for example, in U.S. Pat. Nos. 3,341,331; 3,253,924; 3,384,657; 2,778,658; 2,908,573, 3,227,550; 2,875,057 and 3,551,155, German Patent Application (OLS) No. 1,547,868, U.S. Pat. Nos. 3,265,506; 3,582, 322 and 3,725,072, German Patent Application (OLS) No. 2,162,899, U.S Pat. Nos. 3,369,895; 3,227,155; 3,447,928; 3,415,652, and 3,408,194, German Patent Application (OLS) Nos. 2,057,941; 2,213,461; 2,219,917; 2,261,361 and 2,263,875, and the like.

Typical examples of suitable yellow couplers which can be used include the following couplers

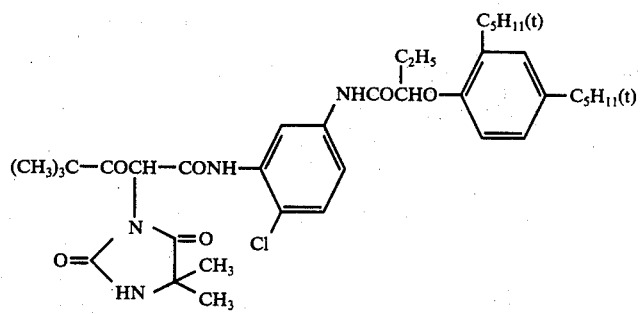

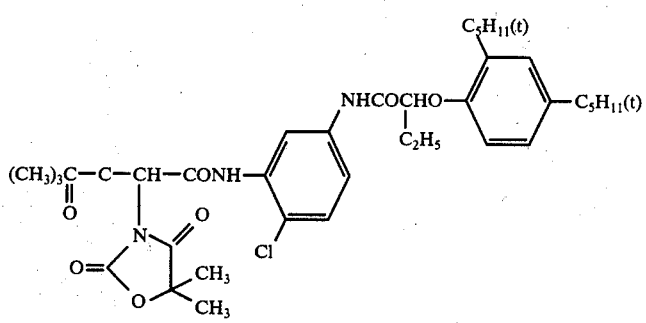

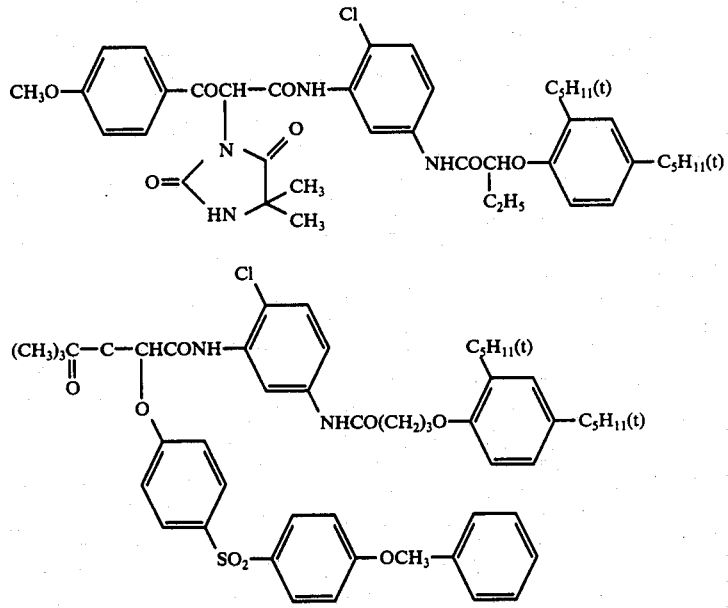

A phenol or naphthol derivative is conventionally used as a cyan coupler. Examples of such compounds are described, for example, in U.S. Pat. Nos. 2,369,929; 2,474,293; 2,908,573; 3,619,196; 3,253,294; 3,227,550; 3,419,390; 3,476,563; 2,698,794; 2,895,826; 3,311,476; 3,458,315; 2,423,730; 2,801,171; 3,046,129; 3,516,831; 2,772,162; 3,560,212; 3,582,322; 3,591,383; 3,386,301; 3,632,347; 3,652,286; 3,779,763; 2,434,272; 2,706,684; 3,034,892 and 3,583,971, German Patent Application (OLS) Nos. 2,163,811 and 2,207,468, Japanese Patent Publication Nos. 28836/1970 and 27563/1964, Japanese Patent Application No. 33238/1973, and the like. Typical examples of suitable cyan couplers which can be used include the following couplers

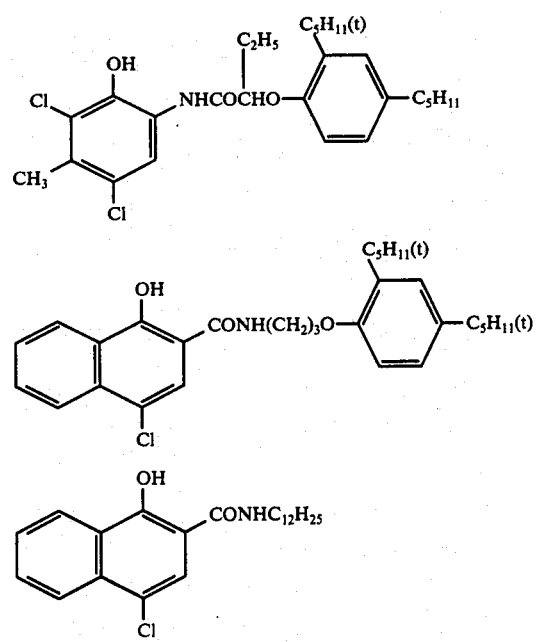

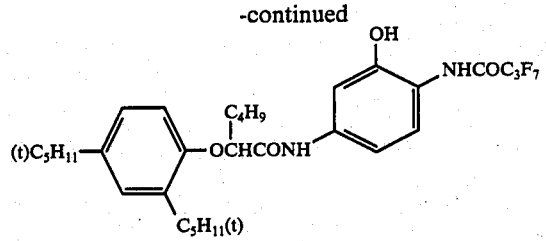

The color photographic light-sensitive material according to the present invention can contain, in a protective layer, an intermediate layer, an emulsion layer or a backing layer, an ultraviolet absorbing agent as described, for example, in U.S. Pat. Nos. 2,685,512; 2,739,888; 2,784,087; 3,253,921; 3,533,794; 3,738,837 and 3,754,919, and the like.

The photographic emulsion can be coated on a substantially planar material which does not undergo severe dimensional change during processing including a rigid support such as glass, metal or ceramics, or a flexible support as desired. Representative flexible supports include those generally used for photographic light-sensitive materials, such as a cellulose nitrate film, a cellulose acetate film, a cellulose acetate butyrate film, a cellulose acetate propionate film, a polystyrene film, a polyethylene terephthalate film, a polycarbonate film, a laminate of these polymers, a thin glass film and a paper. A baryta coated paper, a paper which is coated or laminated with an α-olefin polymer, particularly those obtained from an α-olefin monomer having from 2 to 10 carbon atoms, such as polyethylene, polypropylene and ethylene-butene copolymers, and a synthetic resin film in which the adhesiveness to other polymers and the printing properties are improved by roughening its surfaces, such as is described in Japanese Patent Publication No. 19068/1972, can also be used to advantage as a support.

These supports can be transparent or opaque, depending on the end-use purpose of the photographic materials. Colored transparent supports which contain a dye or a pigment can also be used.

Examples of opaque supports include films produced by incorporating into a transparent film a dye or a pigment such as titanium oxide or surface-treated synthetic resin films such as those described in Japanese Patent Publication No. 19068/1972, as well as intrinsically opaque materials such as paper. Highly light-shielding papers and synthetic resin films containing, for example, carbon black or dyes can also be employed. When the adhesion between a support and a photographic layer is unsatisfactory, a subbing layer which adheres well to both the support and the photographic layer can be provided on the support. The surfaces of the supports can also be pre-treated using a corona discharge, a UV radiation treatment, a flame treatment and the like in order to further improve the adhesiveness. A suitable silver halide coating amount in one emulsion layer can range from about $5 \times 10^{-5}$ to $10^{-6}$ mole/m².

The color photographic light-sensitive materials of the present invention are, after exposure, subjected to a color processing sing to form dye images. The color processing includes basically a color development step, a bleaching step and a fixing step. Each step can be carried out individually or two or more steps can be combined into one step where a processing solution having these two or more functions is used. On example of such a combined bath is a blix solution. Also each step can be separated into two or more steps. For example, a process comprising a color development step, a first fixing step and a blixing step can be used. The color processing can further include a prehardening step, a neutralization step, a first development (black and white development) step, a stabilizing step, a washing step, and the like, if desired. The temperature of processing can be varied depending on the photographic light-sensitive material, the color processing method, and the like. In general, a temperature above about 18° C is used, although a temperature below 18° C can be used. A temperature range of about 20° to 60° C, recently about 30° to 60° C, is conventionally used. These steps need not be necessarily conducted at the same temperature.

A color developer solution is an alkaline solution having a pH or more than about 8, preferably from 9 to 12, and containing, as a developing agent, a compound whose oxidized product is capable of forming a colored compound when reacted with a color forming agent, i.e. a color coupler.

The developing agent described above includes a compound capable of developing an exposed silver halide and having a primary amino group on an aromatic ring, and a precursor which can form such compound. Preferred typical examples of these developing agents are, for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and the salts (for example, the sulfates, the hydrochlorides, the sulfites, the p-toluenesulfonates, and the like) thereof. Other developing agents such as those described in U.S. Pat. Nos. 2,193,015 and 2,592,364, Japenese Patent Application (OPI) No. 64933/1973, and L.F.A. Mason, *Photographic Processing Chemistry*, pages 226 to 229, Focal Press, London (1966). Also 3-pyrazolidones can be used together with these developing agents.

The color developer solution can optionally contain various additives. Typical examples of such additives include alkaline agents (for example, the hydroxides, carbonates or phosphates of alkali metals or ammonia); pH-adjusting agents or buffers (for example, weak acids such as acetic acid, boric acid, etc., weak bases, or salts thereof); developing accelerators (for example, various pyridinium compounds or cationic compound such as those described in U.S. Pat. Nos. 2,648,604 and 3,671,247; potassium nitrate; sodium nitrate; condensation products of polyethylene glycol, and their derivatives such as those described in U.S. Pat. Nos. 2,533,990; 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrozines and the like); anti-fogging agents (for example, alkali metal bromides, alkali metal iodides, nitrobenzimidazoles such as those described in U.S. Pat. Nos. 2,496,940 and 2,656,271, mercaptobenzimidazole, 5-methylbenzotriazole, 1-phenyl-5-mercaptotetrazole, compounds for use in rapid processing solutions such as those described in U.S. Pat. Nos. 3,113,864; 3,342,596; 3,295,976; 3,615,522 and 3,597,119, thiosulfonyl compounds such as those described in British Pat. No. 972,211, phenazine-N-oxides such as those described in Japenese Patent Publication No. 41675/1971, those described in *Kagaku Shashin Binran* (*Manual of Scientific Photography*), Vol. II, pages 29–47, and the like); stain or sludge preventing agents such as those described in U.S. Pat. Nos. 3,161,513 and 3,161,514 and British Pat. Nos. 1,030,422; 1,144,481 and 1,251,558; interlayer-effect accelerators disclosed in U.S. Pat. No. 3,536,487; preservatives (for example, sulfites, bisulfites, hydroxylamine hydrochloride, formsulfite, alkanolamine-sulfite adducts, etc.), and the like.

After color development, the light-sensitive material of the present invention is subjected to a bleaching step in a conventional manner. The bleaching step can be carried out individually or in combination with a fixing step. The bleaching solution can contain a fixing agent to form a blix bath, if desired. Many kinds of compounds are known as a bleaching agent. Of these compounds, ferricyanides; dichromates; water-soluble cobalt (III) salts; water-soluble copper (II) salts; water-soluble quinones; nitrosophenols; complex salts of a polyvalent cation such as iron (III), cobalt (III), and copper (II) and an organic acid, for example, an aminopolycarboxylic acid such as ethylenediamine tetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, etc; a copper complex of 2,6-dipicolinic acid; peracids such as alkylperacids, persulfates, permanganates and peroxides; hypochlorites; chlorine; bromine, and the like can be suitably used, individually or in combination. Bleaching acdelerators such as those described in U.S. Pat. Nos. 3,042,520 and 3,241,966, Japanese Patent Publication Nos. 8506/1970 and 8836/1970 and other various additives can be added to the bleaching solution.

The formation of dye images according to the present invention can be achieved in light-sensitive materials of various forms. In one form, a light-sensitive material having a silver halide emulsion layer containing a diffusion resistant coupler on a support is processed with an alkaline developer solution containing an aromatic primary amine color developing agent to form a water insoluble or diffusion resistant dye in the emulsion layer. In another form, a light-sensitive material having a silver halide emusion layer in combination with a diffusion resistant coupler on a support is processed with an alkaline developer solution containing an aromatic primary amine color developing agent to form a dye soluble and diffusable in an aqueous medium and in which the dye is then transferred to another receiving hydropilic colloid layer. This is a diffusion transfer color system. In still another form, a light-sensitive material having a silver halide emulsion layer is treated with an alkaline developer solution containing an aromatic primary amine color developing agent and a coupler dissolved therein to form a water insoluble or diffusion resistant dye in the emulsion layer. This is a coupler-in-the-developer type system. For example, Coupler (8) described above can be used for the second form, Coupler (4) described above can be used for the third form, while the other couplers described above can be used for the first form.

The color photographic light-sensitive material of the present invention includes a color negative film, a color positive film, a color reversal film, a color printing paper and other color photograhic light-sensitive materials, for example a color direct positive light-sensitive material, a light-sensitive material for the color diffusion transfer process, a monochromatic light-sensitive material, and the like.

Also, the photographic light-sensitive material containing the coupler of the present invention can be suitably employed in a method in which developed silver formed by color development is halogenation-bleached and then color developed again to increase the amount of dye formed, such as is described, for example, in U.S. Pat. Nos. 2,439,901; 2,623,822; 2,814,565 and 3,372,028 or to a method in which the silver halide content in a light-sensitive material is reduced using a color intensification method as described in Japanese Patent Application (OPI) No. 9728/1973.

Advantageous results are obtained according to the present invention, some of which are described below.

1. The amount of silver required to provide a certain magenta color image density can be reduced, thus permitting a reduction in the thickness of the light-sensitive layer containing the coupler and improving the sharpness of the image.

2. The heat resistance of the magenta color image formed is improved using the coupler of the present invention.

3. A reduction in the production cost of the light-sensitive material is achieved by the ability to use a reduced amount of silver halide.

4. Magenta couplers which are more stable to chemical compounds such as formaldehyde or acetone are provided.

5. Couplers having a high coupling reactivity are provided.

6. A color image having a lesser extent of fog and stain and superior photograhic properties is obtained.

7. A silver halide color photographic light-sensitive material having a good stability under storage is obtained using the coupler of the present invention.

8. The conversion yield into a dye is improved using the coupler of the present invention.

The present invention will be further explained by reference the following examples.

EXAMPLE 1

A mixture of 26.2 g of Coupler (11) of the present invention, 24 ml of dioctyl butyl phosphate and 60 ml of ethyl acetate was heated at 60° C and the resulting solution was added to 250 ml of an aqueous solution containing 25 g of gelatin and 0.75 of sodium dodecylbenzenesulfonate at 60° C, followed by vigorour mechanical stirring using a homogenizer, thus obtaining a coupler dispersion. The resulting coupler dispersion was mixed with 200 g of a photographic emulsion containing 11.2 × $10^{-2}$ mol of silver chlorobromide (silver bromide: 45 mol%; silver chloride: 55 mol%) and 20 g of gelatin and, after 10 ml of a 3% acetone solution of triethylenephosphoramide as a hardener was added thereto, the final pH was adjusted to 6.5. The mixture was coated onto a cellulose triacetate film support in a dry thickness of 4.5 microns (Film A). This film contained, per m², 1.55 × $10^{-3}$ mol of the coupler and 6.2 × $10^{-3}$ mol of silver chlorobromide.

For comparison, 19.6 g of 1-(2,4,6-trichlorophenyl)-3-{3-[α-(2,4-di-tert-amylphenoxy)butyramido]benzamido}-5-oxo-2-pyrazoline (Comparison Coupler A) as a corresponding comparison coupler in which the coupling position was not substituted was dispersed, in place of the above described Coupler (11), in a manner analogous to the above described coupler, mixed with 400 g of the same emulsion as described above and coated onto a cellulose triacetate film support in a dry thickness of 5.1 microns (Film B). This film contained, per m², 1.57 × $10^{-3}$ mol of the coupler and 12.6 × $10^{-3}$ mol of silver chlorobromide.

These films were subjected to stepwise exposure and then to the following processing.

| Color Processing Step | | |
|---|---|---|
| 1. Color Development | 21° C | 12 min. |
| 2. Water Washing | " | 30 sec. |
| 3. First Fixing | " | 4 min. |
| 4. Water Washing | " | 4 min. |
| 5. Bleaching | " | 8 min. |
| 6. Water Washing | " | 4 min. |
| 7. Second Fixing | " | 4 min. |
| 8. Water Washing | " | 6 min. |
| Color Developer Solution | | (pH 10.7) |
| Sodium Hexametaphosphate | | 2 g |
| Sodium Sulfite (anhydrous) | | 2 g |
| Benzyl Alcohol | | 5 ml |
| Sodium Carbonate (monohydrate) | | 27.5 g |
| Potassium Bromide | | 0.5 g |
| Hydroxylamine Sulfate | | 2.5 g |
| N-Ethyl-N-(β-methanesulfonamidoethyl)-3-methyl-4-aminonaniline Sesquisulfate | | 2.5 g |
| Water to make | | 1 liter |
| Fixing Solution | | (pH 4.5) |
| Sodium Thiosulfate (hexahydrate) | | 80 g |
| Sodium Sulfite (anhydrous) | | 5 g |
| Borax | | 6 g |
| Glacial Acetic Acid | | 4 ml |
| Potassium Alum | | 7 g |
| Water to make | | 1 liter |
| Bleaching Solution | | (pH 7.2) |
| Potassium Ferricyanide | | 100 g |
| Potassium Bromide | | 5 g |
| Boric Acid | | 10 g |
| Borax | | 5 g |
| Water to make | | 1 liter |

After the processings, the optical density of these films was measured with green light to obtain the photographic properties as shown in Table 1. A clear color image was obtained having an absorption maximum of 542 mμ.

Table 1

| Film | Coupler | Coating Amount (mol/m²) Coupler | Coating Amount (mol/m²) AgX | AgX/Coupler (molar ratio) | Thickness (μ) | Fog | Gamma | Relative Sensitivity* | Maximum Color Density |
|---|---|---|---|---|---|---|---|---|---|
| A | (11) | $1.55 \times 10^{-3}$ | $6.2 \times 10^{-3}$ | 4 | 4.5 | 0.02 | 3.10 | 100 | 3.30 |
| B | A | $1.57 \times 10^{-3}$ | $12.6 \times 10^{-3}$ | 8 | 5.1 | 0.02 | 2.10 | 92 | 2.40 |

*Relative sensitivity is the quantity of exposure necessary for providing a density of fog + 0.1

As is evident from the results in Table 1, the coupler of the present invention provided a higher sensitivity and gradation as well as a maximum color density, even when the ratio of silver halide/coupler was decreased to about ½. The above results demonstrate that in using the coupler of the present invention, the quantity of developed silver necessary for obtaining a color image having a certain density can be reduced. That is, the quantities of the coupler and coated silver halide necessary for obtaining a certain maximum color density can be reduced and the developing time can be shortened.

EXAMPLE 2

Using Film A and Film B as described in Example 1, the following processing was carried out:

| Color Processing Step | | |
|---|---|---|
| 1. Color Development | 30° C | 4 min |
| 2. Blixing | " | 2 min |
| 3. Water Washing | " | 2 min |
| 4. Stabilizing Bath | " | 2 min |

The photograhic properties of the thus obtained films are shown in Table 2.

Moreover, as to the Stabilizing Bath, two kinds of stabilizing baths, i.e., Stabilizing Bath (a) which did not contain any formaldehyde and Stabilizing Bath (b) containing 1% of a 40% formaldehyde aqueous solution were prepared. Samples of each of the films were treated with these baths, allowed to stand at 80° C for 1 week and the decreasing ratio of the density based on the initial density was measured and the results obtained are illustrated in Table 3.

| Color Developer Solution | (pH 10.2) |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfonamidoethyl)amino-2-methylaniline Sesquisulfate | 8 g |
| Water to make | 1 liter |
| Blixing Solution | (pH 6.9) |
| Ferric Ethylenediaminetetraacetate | 45 g |
| Ammonium Thiocyanate | 10 g |
| Sodium Sulfite | 10 g |
| Ammonium Thiosulfate (60% aq. soln.) | 100 ml |
| Sodium Ethylenediaminetetraacetate | 5 g |
| Water to make | 1 liter |
| Stabilizing Bath (a) | |
| Tartaric Acid | 10 g |
| Zinc Sulfate | 10 g |
| Sodium Metaborate | 20 g |
| Water to make | 1 liter |
| Stabilizing Bath (b) | |
| Tartaric Acid | 10 g |
| Zind Sulfate | 10 g |
| Sodium Metaborate | 20 g |
| Formaldehyde (40% aq. soln.) | 10 g |
| Water to make | 1 liter |

Table 2

| Film | Coupler | Photographic Property (Stabilizing Bath (a)) Fog | Gamma | Maximum Color Density |
|---|---|---|---|---|
| A | (11) | 0.04 | 3.25 | 3.35 |
| B | A | 0.03 | 2.29 | 2.30 |

Table 3

Durability of Color Image (80° C, standing for one week)

| Film | Stabilizing Bath | Initial Density 0.5 (%) | 1.0 (%) | 2.0 (%) |
|---|---|---|---|---|
| A | a | 10 | 9 | 6 |
|  | b | 9 | 8 | 5 |
| B | a | 57 | 40 | 11 |
|  | b | 11 | 8 | 5 |

The results in Table 2 show that the use of Film A results in a sufficient photographic property even though a strong oxidizer is not used as in the processing of Example 1 and that Film A has superior properties to Film B. The results in Table 3 show that Film A provides sufficient heat durability even though Film A was not subjected to a stabilizing bath treatment containing formaldehyde as in the prior art.

EXAMPLE 3

Onto a baryta paper resin-coated with polyethylene were coated, as a first layer, a blue-sensitive silver chlorobromide emulsion containing α-pivaloyl-α-(2,4-dioxo-5,5-dimethyloxazolidin-3-yl)-2-chloro-5-[α-(2,4-di-tert-amylphenoxy)butyramido]acetanilide in a dry thickness of 3.0 microns (coupler coated amount: $1.18 \times 10^{-3}$ mol/m²; silver coated amount: $3.53 \times 10^{-3}$ mol/m²; silver bromide: 70 mol%, silver chloride: 30 mol%) and further, as a second layer, gelatine containing 2-tert-octylhydroquinone in a dry thickness of 1.5 microns (hydroquinone compound coated amount: 0.05 g/m²).

A mixture of 10.6 g of Coupler (16) of the present invention, 0.8 g of 2,5-di-tert-octylhydroquinone, 0.8 g of 6,6'-dihydroxy-7,7'-dimethyl-4,4,4',4'-tetramethyl-bis-2,2 '-spirochroman, 10 ml of tricresyl phosphate and 30 ml of ethyl acetate was heated and dissolved on a steam bath and added to an aqueous solution containing 10 g of gelatin and 0.5 of sodium cetylsulfate, followed by vigorous mechanical stirring, thus obtaining a coupler dispersion. This coupler dispersion was mixed with 100 g of a photographic silver halide emulsion containing $4.7 \times 10^{-2}$ mol of silver chlorobromide (silver chloride: 50 mol%; silver bromide: 50 mol%) and 9 g of gelatin, to which 3 ml of a 4% aqueous solution of 2-hydroxy-4,6-dichloro-s-triazine sodium salt as a hardener was than added, and the pH was adjusted to 6.3. The resulting mixture was coated in a dry thickness of 1.9 microns as a third layer (coupler coated amount: 4.7

× 10⁻⁴ mol/m²; silver coated amount: 1.88 × 10⁻³ mol/m²).

Then gelatin containing 2,5-di-tert-octylhydroquinone and as an ultraviolet absorber, 2-(5-chlorobenzotriazol-2-yl)-4-methyl-6-tert-butylphenol and 2-(benzotriazol-2-yl)-4-tert-butylphenol was coated in a dry thickness of 2.5 microns as a fourth layer (hydroquinone compound coated amount: 0.05 g/m²; benzotriazole compound coated amount: 0.4 g/m², each), a red-sensitive silver halide emulsion containing 2-[α-(2,4-di-tert-amylphenoxy)butyramido]-4,6-dichloro-5-methylphenol was coated in a dry thickness of 2.5 microns as a fifth layer (coupler coated amount: 0.98 × 10⁻³ mol/m²; silver coated amount: 2.94 × 10⁻³ mol/m²; silver bromide 50 mol%, silver chloride 50 mol%) and gelatin was then coated in a dry thickness of 1.0 micron as an uppermost layer, thus prepareing a color print paper (Film C).

For comparison, another coupler dispersion was prepared in the same manner as described above but using 8.2 g of a corresponding 4-position unsubstituted comparison coupler, i.e., 1-(2,6-dichloro-4-methoxyphenyl)-3-{3-[α-(2,4-di-tert-amylphenoxy)butyramido]benzamido}-5-oxo-2-pyrazoline (Comparison Coupler B), in place of Coupler (16) in the third layer of Film C, mixed with 200 g of a silver halide emulsion having the same composition and coated in a dry thickness of 3.0 microns as a third layer and thus another color print paper was prepared (Film D). In the third layer, 7.5 × 10⁻⁴ mol of the coupler and 6.0 × 10⁻³ mol of the silver halide were coated per m².

When these samples were subjected to stepwise exposure and processing (Stabilizing Bath (a) ) similar to Example 2 and the reflection density was measured with green light, the photographic properties as shown in Table 4 were obtained. A clear color image of a main wavelength of 542 mµ was obtained.

Table 4

| | | Photographic Property | | | | | | |
|---|---|---|---|---|---|---|---|---|
| | | Coating Amount (mol/m²) | | AgX/ Coupler (molar | Fog | | Relative Sensiti- | Maximum Color |
| Film | Coupler | Coupler | AgX | ratio) | (µ) | Gamma | vity | Density |
| C | (16) | 4.7×10⁻⁴ | 1.88×10⁻³ | 4 | 0.05 | 2.35 | 100 | 2.39 |
| D | B | 7.5×10⁻⁴ | 6.0×10⁻³ | 8 | 0.05 | 2.41 | 97 | 2.35 |

It is apparent from the results in Table 4 that the light-sensitive material using the coupler of the present invention provides similar photographic properties to those of the prior art even through the coating amounts of the coupler and silver halide are reduced.

The light-durability when the thus obtained developed films were exposed for 12 days to a daylight type fluorescent lamp of 30,000 lux through a filter capable of absorbing substantially all ultraviolet light having a wavelength of 400 µ or less, the heat, durability when these films were allowed to stand at 80° C in the dark for 1 week and the humidity durability when these films were stored in the dark at 60° C and 75% RH (Relative Humidity) for 2 weeks as shown by the decreasing ratio of density (%) based on the initial density are shown in Table 5 below.

Table 5

| | | Durability of Color Image (Density Decreasing Ratio %) | | | | | | | | |
|---|---|---|---|---|---|---|---|---|---|---|
| | | Fluorescent Lamp 12 Days Initial Density | | | 80° C, 1 week Initial Density | | | 60° C, 75% RH 2 Weeks Initial Density | | |
| Film | Coupler | 0.5 (%) | 1.0 (%) | 2.0 (%) | 0.5 (%) | 1.0 (%) | 2.0 (%) | 0.5 (%) | 1.0 (%) | 2.0 (%) |
| C | (16) | 16 | 10 | 6 | 8 | 5 | 3 | 7 | 4 | 3 |
| D | A | 22 | 16 | 8 | 57 | 30 | 8 | 20 | 13 | 6 |

It is apparent from these results that in using the coupler of the present invention, an image can be obtained which is durable to heat, light, high temperature and high humidity.

While the invention has been described in detail and with reference to specific embodiments thereof, it will be apparent to one skilled in the art that various changes and modifications can be make therein without departing from the spirit and scope thereof.

What is claimed is:

1. A method of forming images which comprises developing a silver halide photographic light-sensitive material in the presence of a photographic two-equivalent magenta coupler, wherein said magenta coupler is represented by the following general formula (II) or (III)

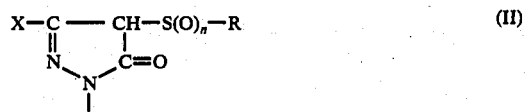

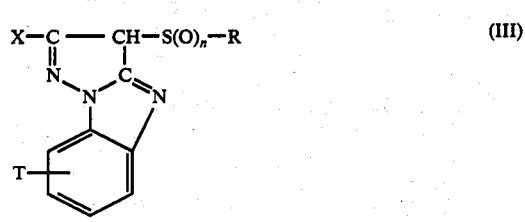

wherein
W represents a hydrogen atom; or has up to 35 carbon atoms and represents a straight chain or branched chain alkyl group, an alkenyl group, a cycloalkyl group, an aralkyl group or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, an ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group and a mercapto group as substituents; an aryl group in which the aryl group can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group as substituents; a heterocyclic group in which the heterocyclic group can be substituted with one or more of the substituents described above for the aryl group for W; an acyl group; a thioacyl group; an alkylsulfonyl group; an arylsulfonyl group; an alkylsulfinyl group; an arylsulfinyl group; a carbamoyl group; or a thiocarbamoyl group;

X represents a hydrogen atom; or has up to 35 carbon atoms and represents a straight chain or branched chain alkyl group, an alkenyl group, a cycloalkyl group, an aralkyl group, a cycloalkenyl group, an aryl group, or a heterocyclic group, in which each of these groups can be substituted with onr or more of the respective substituents as described above for W; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a thioureido group; an alkoxycarbonylamino group; aryloxycarbonylamino group; an alkoxythiocarbonylamino group; an aryloxythiocarbonylamino group; an anilino group; an alkylamino group; a cycloamino group; an alkylcarbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom; or a sulfo group;

T represents a hydrogen atom; or has up to 35 carbon atoms and represents a straight chain or branched chain alkyl group, an alkenyl group, a cycloalkyl group, an aralkyl group, a cycloalkenyl group, an aryl group, or a heterocyclic group, in which each of these groups can be substituted with one or more of the respective substituents as described above for W; a cyano group; an alkoxy group; an aryloxy group; a halogen atom; a carboxy group; an alkoxycarbonyl group; an aryloxycarbonyl group; an acyloxy group; an alkylcarbonyl group; an arylcarbonyl group; an alkylthiocarbonyl group; an arylthiocarbonyl group; a sulfo group; a sulfamoyl group; a carbamoyl group; an acylamino group; a diacyclamino group; a ureido group; a thioureido group; an alkoxycarbonylamino group; an aryloxycarbonylamino group; an alkoxythiocarbonylamino group; an aryloxythiocarbonylamino group; a sulfonamide group; an alkylsulfonyloxy group; an arylsulfonyloxy group; an arylsulfonyl group; an alkylsulfonyl group; an arylthio group; an alkylthio group; an alkylsulfinyl group; an arylsulfinyl group; an alkylamino group; a dialkylamino group; an anilino group; an N-alkylanilino group; an N-arylanilino group; an N-acylanilino group; a hydroxy group; or a mercapto group;

R has up to 40 carbon atoms and represents a straight chain or branched chain alkyl group, an alkenyl group, or an aralkyl group, in which each of these groups can be substituted with one or more of a halogen atom, a nitro group, a carboxy group, an alkoxy group, an alkylamido group, an arylamido group, a sulfamoyl group, a carbamoyl group, a substituted amino group, an alkylthio group, and an arylthio group as substituents; an aryl group in which the aryl group can be substituted with one or more of a halogen atom, an alkyl group having 1 to 20 carbon atoms, an aralkyl group, an alkenyl group, an alkyloxy group, an aryloxy group, a nitro group, a cyano group, a carboxy group, an alkyloxycarbonyl group, an aryloxycarbonyl group, an acyloxy group, an alkylamido group, an arylamido group, a diacylamino group, a sulfamoyl group, a sulfonamido group, a ureido group, a thioureido group, an alkoxycarbonylamino group, an aryloxycarbonylamino group, an alkoxythiocarbonylamino group, an aryloxythiocarbonylamino group, a carbamoyl group, a substituted amino group, an alkylthio group, an arylthio group, a sulfonyl group and a carbonyl group as substituents; and a heterocyclic group in which the heterocyclic group can be substituted with one or more of the substituents as described above for the aryl group for R; and $n$ is 1 or 2.

2. The method as claimed in claim 1, wherein W is a phenyl group in which at least one of the ortho positions is substituted with an alkyl group, an alkoxy group, or a halogen atom.

3. The method as claimed in claim 1, wherein the magenta coupler is selected from the group consisting of 1-(2,4,6-Trichlorophenyl)-3-{3-[(2,4-di-tert-pentylphenoxy)acetamido]benzamido}-4-phenylsulfonyl-5-oxo-2-pyrazoline;

1-(2,4,6-Trichlorophenyl)-3-{3-[α-(3-tert-butyl-4-hydroxyphenoxy)tetradecanamido]benzamido}-4-tetradecylsulfonyl-5-oxo-2-pyrazoline, 2-Heptadecyl-3-(3-ethoxycarbonylphenylsulfonyl)-3H-pyrazolo-[1,5-a]-benzimidazole, 1-(2,4,6-Trichlorophenyl)-3-methoxy-4-(2-ethoxycarbonylphenylsulfonyl)-5-oxo-2-pyrazoline, 1-(2-Chloro-4,6-dimethylphenyl)-3-{2-chloro-4-[γ-(2,4-di-tert-pentylphenoxy)propylsulfamoyl-]anilino}-4-(3-nitrophenylsulfonyl-5-oxo-2-pyrazoline, 1-(2,4,6-Trichlorophenyl)-3-[(3-n-octadecylsuccinimido)-benzamido]-4-phenylsulfinyl-5-oxo-2-pyrazoline, 1-(2,6-Dichloro-4-methoxyphenyl)-3-{3-[α-(2,4-di-tert-pentylphenoxy)butyramido]benzamido}-4-tetradecylsulfonyl-5-oxo-2-pyrazoline, 1-(2,4,6-Trichlorophenyl)-3-(3,5-dicarboxyanilino)-4-(3-octadecylcarbamoylphenylsulfonyl)-5-oxo-2-pyrazoline 2-[3-(α-Octyloxymethylpropylamido)benzamido]-3-phenylsulfinyl-7-chloro-3H-pyrazolo-[1,5-a]-benzimidazole, 1-(3-Sulfo-4-phenoxyphenyl)-3-n-octadecyl-4-phenylsulfonyl-5-oxo-2-pyrazoline, 1-(2,4,6-Trichlorophenyl)-3-{3-[α-(2,4-di-tert-pentylphenoxy)butyramido]benzamido}-4-dodecylsulfonyl-5-oxo-2-pyrazoline, 1-(2,4,6-Trichlorophenyl)-3-[(2-chloro-5-tetradecanamido)-anilino]-4-(3-acetylaminophenylsulfonyl)-5-oxo-2-pyrazoline, 1-{4-[(2,4-Di-tert-pentylphenoxy)acetamido]phenyl}-3-(2,4-dichloroanilino)-4-phenylsulfonyl-5-oxo-2-pyrazoline, 1-(2,4,6-Trichlorophenyl)-3-{3-[α-(2,4-di-tert-pentylphenoxy)butyramido]phenylureido}-4-(2-pyridylsulfonyl)-5-oxo-2-pyrazoline, 1-(2,4,6-Trichlorophenyl)-3-[2-chloro-5-(2-carboxymethyl-2-nonadecenylamido)anilino]-4-(1-naphthylsulfonyl)-5-oxo-2-pyrazoline, and 1-(2,6-Dichloro-4-methoxyphenyl)-3-{3-[α-(2,4-di-tert-pentylphenoxy)butyramido]benzamido}-4-(2-ethoxycarbonylphenylsulfonyl)-5-oxo-2-pyrazoline, 4. A photographic silver halide emulsion containing a photographic two-equivalent magenta coupler wherein said magenta coupler is represented by the following general formula (II) or (III)

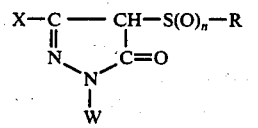
(II)

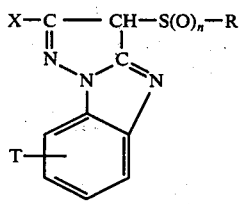
(III)

wherein
W represents a hydrogen atom; or has up to 35 carbon atoms and represents a straight chain or branched chain alkyl group, an alkenyl group, a cycloalkyl group, an aralkyl group or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, an ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, arylsulfinyl group, an alkylamino group, a dialkylamino group, an anilino group, an N-arylanilino group, an N-alkylanilino group, an N-acylanilino group, a hydroxy group and a mercapto group as substituents; an aryl group in which the aryl group can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group as substituents; a heterocyclic group in which the heterocyclic group can be substituted with one or more of the substituents described above for the aryl group for W; and acyl group; a thioacyl group; an alkylsulfonyl group; an arylsulfonyl group; an alkylsulfinyl group; an arylsulfinyl group; a carbamoyl group; or a thiocarbamoyl group;

X represents a hydrogen atom; or has up to 35 carbon atoms and represents a straight chain or branched chain alkyl group, an alkenyl group, a cycloalkyl group, an aralkyl group, a cycloalkenyl group, an aryl group, or a heterocyclic group, in which each of these groups can be substituted with one or more of the respective substituents as described above for W; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a thioureido group; an alkoxycarbonylamino group; an aryloxycarbonylamino group; an alkoxythiocarbonylamino group; an aryloxythiocarbonylamino group; an anilino group; an alkylamino group; a cycloamino group; an alkylcarbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom; or a sulfo group;

T represents a hydrogen atom; or has up to 35 carbon atoms and represents a straight chain or branched chain alkyl group, an alkenyl group, a cycloalkyl group, an aralkyl group, a cycloalkenyl group, an aryl group, or a heterocyclic group, in which each of these groups can be substituted with one or more of the respective substituents as described above for W; a cyano group; an alkoxy group; an aryloxy group; a halogen atom; a carboxy group; an alkoxycarbonyl group; an aryloxycarbonyl group; an acyloxy group; an alkylcarbonyl group; an arylcarbonyl group; an alkylthiocarbonyl group; an arylthiocarbonyl group; a sulfo group; a sulfamoyl group; a carbamoyl group; an acylamino group; a diacylamino group; a ureido group; a thioureido group; an alkoxycarbonylamino group; an aryloxycarbonylamino group; an alkoxythiocarbonylamino group; an aryloxythiocarbonylamino group; a sulfonamido group; an alkylsulfonyloxy group; an arylsulfonyloxy group; an arylsulfonyl group; an alkylsulfonyl group; an arylthio group; an alkylthio group; an alkylsulfinyl group; an arylsulfinyl group; an alkylamino group; a dialkylamino group; an anilino group; an N-alkylanilino group; an N-arylanilino group; an N-acylanilino group; a hydroxy group; or a mercapto group;

R has up to 40 carbon atoms and represents a straight chain or branched chain alkyl group, an alkenyl group, or an aralkyl group, in which each of these groups can be substituted with one or more of a halogen atom, a nitro group, a carboxy group, an alkoxy group, an alkylamido group, an arylamido group, a sulfamoyl group, a carbamoyl group, a substituted amino group, an alkylthio group, and an arylthio group as substituents; an aryl group in which the aryl group can be substituted with one or more of a halogen atom, an alkyl group having 1 to 20 carbon atoms, an aralkyl group, an alkenyl group, an alkyloxy group, an aryloxy group, a nitro group, a cyano group, a carboxy group, an alkyloxycarbonyl group, an aryloxycarbonyl group, an acyloxy group, an alkylamido group, an arylamido group, a diacylamino group, a sulfamoyl group, a sulfonamido group, a ureido group, a thioureido group, an alkoxycarbonylamino group, an aryloxycarbonylamino group, an alkoxythiocarbonylamino group, an aryloxythiocarbonylamino group, a carbamoyl group, a substituted amino group, an alkylthio group, an arylthio group, a sulfonyl group and a carbonyl group as substituents; and a heterocyclic group in which the heterocyclic group can be substituted with one or more of the substituents as described above for the aryl group for R; and n is 1 or 2.

5. The photographic silver halide emulsion as claimed in claim 4, wherein W is a phenyl group in which at least one of the ortho positions is substituted with an alkyl group, an alkoxy group, or a halogen atom.

6. The photographic silver halide emulsion as claimed in claim 4, wherein said magenta coupler is selected from the group consisting of
1-(2,4,6-Trichlorophenyl)-3-{3-[(2,4-di-tert-pentylphenoxy)acetamido]benzamido}-4-phenylsulfonyl-5-oxo-2-pyrazoline.
1-(2,4,6-Trichlorophenyl)-3-{3-[α-(3-tert-butyl-4-hydroxyphenoxy)tetradecanamido]benzamido}-4-tetradecylsulfonyl-5-oxo-2-pyrazoline,
2-Heptadecyl-3-(3-ethoxycarbonylphenylsulfonyl)-3H-pyrazolo-[1,5-a]-benzimidazole,
1-(2,4,6-Trichlorophenyl)-3-methoxy-4-(2-ethoxycarbonylphenylsulfonyl)-5-oxo-2-pyrazoline,
1-(2-Chloro-4,6-dimethylphenyl)-3-{2-chloro-4-γ-(2,4-di-tert-pentylphenoxy)propylsulfamoyl]anilino}-4-(3-nitrophenylsulfonyl-5-oxo-2-pyrazoline,
1-(2,4,6-Trichlorophenyl)-3-[(3-n-octadecylsuccinimido)benzamido]-4-phenylsulfinyl-5-oxo-2-pyrazoline,
1-(2,6-Dichloro-4-methoxyphenyl)-3-{3-[α-(2,4-di-tert-pentylphenoxy)butyramido]benzamido}-4-tetradecylsulfonyl-5-oxo-2-pyrazoline,
1-(2,4,6-Trichlorophenyl)-3-(3,5-dicarboxyanilino)-4-(3-octadecylcarbamoylphenylsulfonyl)-5-oxo-2-pyrazoline,
2-[3-(α-Octyloxymethylpropylamido)benzamido]-3-phenylsulfinyl-7-chloro-3H-pyrazolo-[1,5-a]-benzimidazole,
1-(3-Sulfo-4-phenoxyphenyl)-3-n-octadecyl-4-phenylsulfonyl 5-oxo-2-pyrazoline,
1-(2,4,6-Trichlorophenyl)-3-{3-[α-(2,4-di-tert-pentylphenoxy)butyramido]benzamido}-4-dodecylsulfonyl-5-oxo-2-pyrazoline,
1-(2,4,6-Trichlorophenyl)-3-[(2-chloro-5-tetradecanamido)anilino]-4-(3-acetylaminophenylsulfonyl)-5-oxo-2-pyrazoline,
1-{4-[(2,4-Di-tert-pentylphenoxy)acetamido]phenyl}-3-(2,4-dichloroanilino)-4-phenylsulfonyl-5-oxo-2-pyrazoline,
1-(2,4,6)-Trichlorophenyl)-3-{3-[α-(2,4-di-tert-pentylphenoxy)butyramido]phenylureido}-4-(2-pyridylsulfonyl)-5-oxo-2-pyrazoline.
1-(2,4,6-Trichlorophenyl)-3-[2-chloro-5-(2-carboxymethyl-2-nonadecenylamido)anilino]-4-(1-naphthylsulfonyl)-5-oxo-2-pyrazoline, and
1-(2,6-Dichloro-4-methoxyphenyl)-3-{3-[α-(2,4-di-tert-pentylphenoxy)butyramido]benzamido}-4-(2-ethoxycarbonylphenylsulfonyl)-5-oxo-2-pyrazoline.

7. A photographic light-sensitive material comprising a support having thereon a photographic silver halide emulsion containing a two-equivalent magneta coupler wherein said magenta coupler is represented by the following general formula (II) or (III)

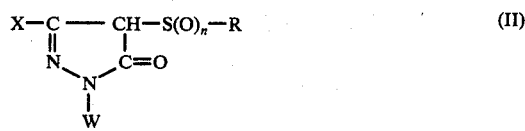

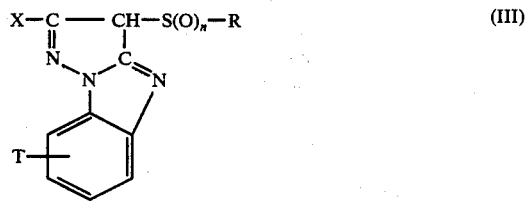

wherein
W represents a hydrogen atom; or has up to 35 carbon atoms and represents a straight chain or branched chain alkyl group, an alkenyl group, a cycloalkyl group, an aralkyl group or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, an ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, arylsulfinyl group, an alkylamino group, a dialkylamino group, an anilino group, an N-arylanilino group, an N-alkylanilino group, an N-acylanilino group, a hydroxy group and a mercapto group as substituents; an aryl group in which the aryl group can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group as substituents; a heterocyclic group in which the heterocyclic group can be substituted with one or more of the substituents described above for the aryl group for W; an acyl group; a thioacyl group; an alkylsulfonyl group; an arylsulfonyl group; an alkylsulfinyl group; an arylsulfinyl group; a carbamoyl group; or a thiocarbamoyl group;

X represents a hydrogen atom; or has up to 35 carbon atoms and represents a straight chain or branched chain alkyl group, an alkenyl group, a cycloalkyl group, an aralkyl group, a cycloalkenyl group, an aryl group, or a heterocyclic group, in which each of these groups can be substituted with one or more of the respective substituents as described above for W; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a thioureido group; an alkoxycarbonylamino group; an aryloxycarbonylamino group; an alkoxythiocarbonylamino group; an aryloxythiocarbonylamino group; an anilino group; an alkylamino group; a cycloamino group; an alkylcarbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom; or a sulfo group;

T represents a hydrogen atom; or has up to 35 carbon atoms and represents a straight chain or branched chain alkyl group, an alkenyl group, a cycloalkyl group, an aralkyl group, a cycloalkenyl group, an aryl group, or a heterocyclic group, in which each of these groups can be substituted with one or more of the respective substituents as described above for W; a cyano group; an alkoxy group; an aryloxy group; a halogen atom; a carboxy group; an alkoxycarbonyl group; an aryloxycarbonyl group; an acyloxy group; an alkylcarbonyl group; an arylcarbonyl group; an alkylthiocarbonyl group; an arylthiocarbonyl group; a sulfo group; a sulfamoyl group; a carbamoyl group; an acylamino group; a diacylamino group; a ureido group; a thioureido group; an alkoxycarbonylamino group; an aryloxycarbonylamino group; an alkoxythiocarbonylamino group; an aryloxythiocarbonylamino group; a sulfonamido group; an alkylsulfonyloxy group; an arylsulfonyloxy group; an arylsulfonyl group; an alkylsulfonyl group; an arylthio group; an alkylthio group; an alkylsulfinyl group; an arylsulfinyl group; an alkylamino group; a dialkylamino group; an anilino group; an N-alkylanilino group; an N-arylanilino group; an N-acylanilino group; a hydroxy group; or a mercapto group;

R has up to 40 carbon atoms and represents a straight chain or branched chain alkyl group, an alkenyl group, or an aralkyl group, in which each of these groups can be substituted with one or more of a halogen atom, a nitro group, a carboxy group, an alkoxy group, an alkylamido group, an arylamido group, a sulfamoyl group, a carbamoyl group, a substituted amino group, an alkylthio group, and an arylthio group as substituents; an aryl group in which the aryl group can be substituted with one or more of a halogen atom, an alkyl group having 1 to 20 carbon atoms, an aralkyl group, an alkenyl group, an alkyloxy group, an aryloxy group, a nitro group, a cyano group, a carboxy group, an alkyloxycarbonyl group, an aryloxycarbonyl group, an acyloxy group, an alkylamido group, an arylamido group, a diacylamino group, a sulfamoyl group, a sulfonamido group, a ureido group, a thioureido group, an alkoxycarbonylamino group, an aryloxycarbonylamino group, an alkoxythiocarbonylamino group, an aryloxythiocarbonylamino group, a carbamoyl group, a substituted amino group, an alkylthio group, an arylthio group, a sulfonyl group and a carbonyl group as substituents; and a heterocyclic group in which the heterocyclic group can be substituted with one or more of the substituents as described above for the aryl group for R; and $n$ is 1 or 2.

8. The light-sensitive material of claim 7, wherein W is a phenyl group in which at least one of the ortho positions is substituted with an alkyl group, an alkoxy group or a halogen atom.

9. The light-sensitive material of claim 7, wherein said support has thereon a blue-sensitive silver halide emulsion layer, a green-sensitive layer of said photographic silver halide emulsion containing a two-equivalent magenta coupler as described in claim 7 and a red-sensitive silver halide emulsion layer.

10. The light-sensitive material of claim 7, wherein said magenta coupler is selected from the group consisting of 1-(2,4,6-Trichlorophenyl)-3-{3-[(2,4-di-tert-pentylphenoxy)acetamido]benzamido}-4-phenylsulfonyl-5-oxo-2-pyrazoline, 1-(2,4,6-Trichlorophenyl)-3-{3-[α-(3-tert-butyl-4-hydroxyphenoxy)tetradecanamido]benzamido}-4-tetradecylsulfonyl-5-oxo-2-pyrazoline, 2-Heptadecyl-3-(3-ethoxycarbonylphenylsulfonyl)-3H-pyrazolo-[1,5-a]-benzimidazole, 1-(2,4,6-Trichlorophenyl)-3-methoxy-4-(2-ethoxycarbonylphenylsulfonyl)-5-oxo-2-pyrazoline, 1-(2-Chloro-4,6-dimethylphenyl)-3-{2-chloro-4-γ-(2,4-di-tert-pentylphenoxy)propylsulfamoyl]anilino}-4-(3-nitrophenylsulfonyl-5-oxo-2-pyrazoline, 1-(2,4,6-Trichlorophenyl)-3-[(3-n-octadecylsuccinimido)benzamido]-4-phenylsulfinyl-5-oxo-2-pyrazoline, 1-(2,6-Dichloro-4-methoxyphenyl)-3-{3-[α-(2,4-di-tert-pentylphenoxy)butyramido]benzamido}-4-tetradecylsulfonyl-5-oxo-2-pyrazoline, 1-(2,4,6-Trichlorophenyl)-3-(3,5-dicarboxyanilino)-4-(3-octadecylcarbamoylphenylsulfonyl)-5-oxo-2-pyrazoline, 2-[3-(α-Octyloxymethylpropylamido)benzamido]-3-phenylsulfinyl-7-chloro-3H-pyrazolo-[1,5-a]-benzimidazole, 1-(3-Sulfo-4-phenoxyphenyl)-3-n-octadecyl-4-phenylsulfonyl 5-oxo-2-pyrazoline, 1-(2,4,6-Trichlorophenyl)-3-{3-[α-(2,4-di-tert-pentylphenoxy)butyramido]benzamido}-4-dodecylsulfonyl-5-oxo-2-pyrazoline, 1-(2,4,6-Trichlorophenyl)-3-[(2-chloro-5-tetradecanamido)anilino]-4-(3-acetylaminophenylsulfonyl)-5-oxo-2-pyrazoline, 1-{4-[(2,4-Di-tert-pentylphenoxy)acetamido]phenyl}-3-(2,4-dichloroanilino)-4-phenylsulfonyl-5-oxo-2-pyrazoline, 1-(2,4,6-Trichlorophenyl)-3-{3-[α-(2,4-di-tert-pentylphenoxy)butyramido]phenylureido}-4-(2-pyridylsulfonyl)-5-oxo-2-pyrazoline, 1-(2,4,6-Trichlorophenyl)-3-[2-chloro-5-(2-carboxymethyl-2-nonadecenylamido)anilino]-4-(1-naphthylsulfonyl)-5-oxo-2-pyrazoline, and 1-(2,6-Dichloro-4-methoxyphenyl)-3-{3-[(α-(2,4,-di-tert-pentylphenoxy)butyramido]benzamido}-4-(2-ethoxycarbonylphenylsulfonyl)-5-oxo-2-pyrazoline,

* * * * *